United States Patent
Chuang et al.

(10) Patent No.: US 9,601,299 B2
(45) Date of Patent: Mar. 21, 2017

(54) PHOTOCATHODE INCLUDING SILICON SUBSTRATE WITH BORON LAYER

(71) Applicant: KLA-Tencor Corporation, Milpitas, CA (US)

(72) Inventors: Yung-Ho Alex Chuang, Cupertino, CA (US); John Fielden, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 380 days.

(21) Appl. No.: 13/947,975

(22) Filed: Jul. 22, 2013

(65) Prior Publication Data

US 2014/0034816 A1 Feb. 6, 2014

Related U.S. Application Data

(60) Provisional application No. 61/679,200, filed on Aug. 3, 2012.

(51) Int. Cl.
H01J 5/16 (2006.01)
H01J 29/38 (2006.01)
(Continued)

(52) U.S. Cl.
CPC ........ H01J 29/385 (2013.01); G01N 21/9501 (2013.01); G02B 21/125 (2013.01);
(Continued)

(58) Field of Classification Search
CPC .. H01J 29/395; H01J 29/44; H01J 9/45; H01J 29/451; H01J 29/453; H01J 29/455;
(Continued)

(56) References Cited

U.S. PATENT DOCUMENTS 3,755,704 A 8/1973 Spindt et al.
3,870,917 A 3/1975 Cuny
(Continued)

FOREIGN PATENT DOCUMENTS

EP 0746871 B1 5/2000
EP 0602983 B1 6/2000
(Continued)

OTHER PUBLICATIONS

Allen, F. G. et al. "Work Function, Photoelectric Threshold, and Surface States of Atomicaly Clean Silicon", Physical Review, vol. 127. No. 1, Jul. 1, 1962, pp. 150-158.
(Continued)

Primary Examiner — Thanh Luu
Assistant Examiner — Kevin Wyatt
(74) Attorney, Agent, or Firm — Bever, Hoffman & Harms, LLP

(57) ABSTRACT

A photocathode is formed on a monocrystalline silicon substrate having opposing illuminated (top) and output (bottom) surfaces. To prevent oxidation of the silicon, a thin (e.g., 1-5 nm) boron layer is disposed directly on the output surface using a process that minimizes oxidation and defects, and a low work-function material layer is then formed over the boron layer to enhance the emission of photoelectrons. The low work-function material includes an alkali metal (e.g., cesium) or an alkali metal oxide. An optional second boron layer is formed on the illuminated (top) surface, and an optional anti-reflective material layer is formed on the boron layer to enhance entry of photons into the silicon substrate. An optional external potential is generated between the opposing illuminated (top) and output (bottom) surfaces. The photocathode forms part of novel sensors and inspection systems.

12 Claims, 9 Drawing Sheets

(51) Int. Cl.
   *H01J 1/34*    (2006.01)
   *H01J 31/26*   (2006.01)
   *H01J 31/50*   (2006.01)
   *G02B 21/12*   (2006.01)
   *G01N 21/95*   (2006.01)
   *H01L 27/146*  (2006.01)
   *H01L 27/148*  (2006.01)

(52) U.S. Cl.
   CPC ............. *H01J 1/34* (2013.01); *H01J 31/26* (2013.01); *H01J 31/50* (2013.01); *H01L 27/148* (2013.01); *H01L 27/14643* (2013.01)

(58) Field of Classification Search
   CPC .. H01J 29/385; H01J 1/34; H01J 31/26; H01J 31/50; G02B 21/125; G01N 21/9501
   USPC ............................................ 250/216; 257/10
   See application file for complete search history.

(56) References Cited

U.S. PATENT DOCUMENTS

| | | | |
|---|---|---|---|
| 3,947,707 A * | 3/1976 | Shannon | G03G 5/024 257/257 |
| 4,099,198 A | 7/1978 | Howorth et al. | |
| 4,210,922 A | 7/1980 | Shannon | |
| 4,275,326 A * | 6/1981 | Houtkamp | H01J 9/2278 313/466 |
| 4,348,690 A | 9/1982 | Jastrzebski | |
| 4,467,189 A | 8/1984 | Tsuchiya | |
| 4,555,731 A | 11/1985 | Zinchuk | |
| 4,644,221 A | 2/1987 | Gutierrez et al. | |
| 4,760,031 A | 7/1988 | Janesick | |
| 4,853,595 A | 8/1989 | Alfano et al. | |
| 5,054,683 A | 10/1991 | Haisma et al. | |
| 5,120,949 A | 6/1992 | Tomasetti | |
| 5,227,313 A | 7/1993 | Gluck et al. | |
| 5,315,126 A | 5/1994 | Field | |
| 5,376,810 A | 12/1994 | Hoenk et al. | |
| 5,563,702 A | 10/1996 | Emery et al. | |
| 5,717,518 A | 2/1998 | Shafer et al. | |
| 5,719,069 A | 2/1998 | Sparks | |
| 5,731,584 A | 3/1998 | Beyne | |
| 5,742,626 A | 4/1998 | Mead et al. | |
| 5,760,809 A | 6/1998 | Malhotra et al. | |
| 5,760,899 A | 6/1998 | Eismann | |
| 5,852,322 A | 12/1998 | Speckbacher | |
| 5,940,685 A | 8/1999 | Loomis et al. | |
| 5,999,310 A | 12/1999 | Shafer et al. | |
| 6,013,399 A | 1/2000 | Nguyen | |
| 6,064,759 A | 5/2000 | Buckley et al. | |
| 6,162,707 A * | 12/2000 | Dinh | C23C 14/08 117/3 |
| 6,201,257 B1 | 3/2001 | Stettner et al. | |
| 6,201,601 B1 | 3/2001 | Vaez-Iravani et al. | |
| 6,220,914 B1 | 4/2001 | Lee et al. | |
| 6,271,916 B1 | 8/2001 | Marxer et al. | |
| 6,278,119 B1 | 8/2001 | Nikzad et al. | |
| 6,285,018 B1 | 9/2001 | Aebi et al. | |
| 6,297,879 B1 | 10/2001 | Yang et al. | |
| 6,307,586 B1 | 10/2001 | Costello | |
| 6,346,700 B1 | 2/2002 | Cunningham et al. | |
| 6,362,484 B1 | 3/2002 | Beyne | |
| 6,373,869 B1 | 4/2002 | Jacob | |
| 6,403,963 B1 | 6/2002 | Nikzad et al. | |
| 6,545,281 B1 | 4/2003 | McGregor | |
| 6,608,676 B1 | 8/2003 | Zhao et al. | |
| 6,711,283 B1 | 3/2004 | Soenksen | |
| 6,837,766 B2 | 1/2005 | Costello | |
| 7,005,637 B2 | 2/2006 | Costello et al. | |
| 7,039,157 B2 | 5/2006 | Fuji et al. | |
| 7,126,699 B1 | 10/2006 | Wihl et al. | |
| 7,130,039 B2 | 10/2006 | Vaez-Iravani et al. | |
| 7,283,166 B1 | 10/2007 | Billman | |
| 7,313,155 B1 | 12/2007 | Mu | |
| 7,345,825 B2 | 3/2008 | Chuang et al. | |
| 7,352,457 B2 | 4/2008 | Kvamme et al. | |
| 7,446,474 B2 | 11/2008 | Maldonado | |
| 7,465,935 B2 | 12/2008 | Urano et al. | |
| 7,525,649 B1 | 4/2009 | Leong et al. | |
| 7,528,943 B2 | 5/2009 | Brown et al. | |
| 7,586,108 B2 * | 9/2009 | Nihtianov | G03F 7/7085 250/372 |
| 7,609,309 B2 | 10/2009 | Brown et al. | |
| 7,741,666 B2 | 6/2010 | Nozaki et al. | |
| 7,750,280 B2 | 7/2010 | Hwang et al. | |
| 7,791,170 B2 | 9/2010 | Chiang et al. | |
| 7,800,040 B2 | 9/2010 | Blacksberg et al. | |
| 7,875,948 B2 | 1/2011 | Hynecek et al. | |
| 7,928,382 B2 | 4/2011 | Hatakeyama et al. | |
| 7,952,633 B2 | 5/2011 | Brown et al. | |
| 7,985,658 B2 | 7/2011 | Lei et al. | |
| 7,999,342 B2 | 8/2011 | Hsu et al. | |
| 8,017,427 B2 | 9/2011 | Manabe | |
| 8,138,485 B2 | 3/2012 | Nihtianov et al. | |
| 8,309,443 B2 | 11/2012 | Tanaka et al. | |
| 8,450,820 B2 | 5/2013 | Nanver | |
| 8,455,971 B2 | 6/2013 | Chen et al. | |
| 8,513,587 B2 | 8/2013 | Wang et al. | |
| 8,514,587 B2 | 8/2013 | Zhang et al. | |
| 8,629,384 B1 | 1/2014 | Biellak et al. | |
| 8,686,331 B2 | 4/2014 | Armstrong | |
| 8,754,972 B2 | 6/2014 | Brown et al. | |
| 8,891,079 B2 | 11/2014 | Zhao et al. | |
| 2001/0017344 A1 | 8/2001 | Aebi | |
| 2002/0191834 A1 | 12/2002 | Fishbaine | |
| 2003/0043876 A1 | 3/2003 | Lublin et al. | |
| 2003/0222579 A1 * | 12/2003 | Habib | B82Y 10/00 313/523 |
| 2004/0021061 A1 | 2/2004 | Bijkerk | |
| 2004/0056279 A1 | 3/2004 | Niigaki | |
| 2004/0227070 A1 | 11/2004 | Bateman et al. | |
| 2005/0122021 A1 | 6/2005 | Smith et al. | |
| 2005/0167575 A1 | 8/2005 | Benz et al. | |
| 2005/0190452 A1 | 9/2005 | Govorkov et al. | |
| 2005/0264148 A1 | 12/2005 | Maldonado et al. | |
| 2006/0054778 A1 | 3/2006 | Suhling | |
| 2006/0055321 A1 | 3/2006 | Maldonado et al. | |
| 2006/0069460 A1 | 3/2006 | Smith et al. | |
| 2006/0170324 A1 | 8/2006 | Machuca | |
| 2007/0002465 A1 | 1/2007 | Chuang et al. | |
| 2007/0034987 A1 | 2/2007 | Costello et al. | |
| 2007/0096648 A1 | 5/2007 | Nakajima et al. | |
| 2007/0103769 A1 | 5/2007 | Kuwabara | |
| 2007/0188744 A1 | 8/2007 | Leslie et al. | |
| 2007/0291810 A1 | 12/2007 | Luo et al. | |
| 2008/0044931 A1 | 2/2008 | Tong et al. | |
| 2008/0182092 A1 | 7/2008 | Bondokov et al. | |
| 2008/0267241 A1 | 10/2008 | Brown et al. | |
| 2008/0315092 A1 | 12/2008 | Kley | |
| 2008/0315121 A1 | 12/2008 | Nihtianov et al. | |
| 2009/0021717 A1 | 1/2009 | Nihtianov et al. | |
| 2009/0091752 A1 | 4/2009 | Terasawa et al. | |
| 2009/0108207 A1 | 4/2009 | Liu | |
| 2009/0125242 A1 | 5/2009 | Choi | |
| 2009/0128912 A1 | 5/2009 | Okada | |
| 2009/0168152 A1 | 7/2009 | Gelernt et al. | |
| 2009/0180176 A1 | 7/2009 | Armstrong et al. | |
| 2009/0261263 A1 * | 10/2009 | Menge | G01V 5/04 250/370.11 |
| 2010/0102213 A1 | 4/2010 | Garris | |
| 2010/0103409 A1 | 4/2010 | Ohshima et al. | |
| 2010/0148667 A1 | 6/2010 | Niigaki et al. | |
| 2010/0301437 A1 | 12/2010 | Brown et al. | |
| 2011/0073982 A1 | 3/2011 | Armstrong et al. | |
| 2011/0101219 A1 | 5/2011 | Uchiyama et al. | |
| 2011/0116077 A1 | 5/2011 | Chuang et al. | |
| 2011/0169116 A1 | 7/2011 | Nanver et al. | |
| 2011/0234790 A1 | 9/2011 | True | |
| 2011/0256655 A1 | 10/2011 | Nikzad et al. | |
| 2011/0261354 A1 | 10/2011 | Sinfield | |
| 2011/0291109 A1 | 12/2011 | Wraback | |
| 2012/0012811 A1 | 1/2012 | DeFlumere | |
| 2012/0012957 A1 | 1/2012 | Larsen | |

(56) References Cited

U.S. PATENT DOCUMENTS

| | | | |
|---|---|---|---|
| 2012/0081684 | A1 | 4/2012 | Den Oef et al. |
| 2012/0132823 | A1 | 5/2012 | Menge |
| 2012/0160993 | A1 | 6/2012 | Nevet |
| 2012/0170021 | A1 | 7/2012 | Walsh |
| 2012/0228485 | A1 | 9/2012 | Iwakiri et al. |
| 2012/0268722 | A1 | 10/2012 | Nihtianov et al. |
| 2013/0009069 | A1 | 1/2013 | Okada |
| 2013/0016346 | A1 | 1/2013 | Romanovsky et al. |
| 2013/0017205 | A1 | 1/2013 | Giaccia et al. |
| 2013/0020491 | A1 | 1/2013 | Mazzillo |
| 2013/0056843 | A1 | 3/2013 | Lee |
| 2013/0077086 | A1 | 3/2013 | Chuang et al. |
| 2013/0082241 | A1 | 4/2013 | Kub et al. |
| 2013/0126705 | A1 | 5/2013 | Maleev |
| 2013/0148112 | A1 | 6/2013 | Chuang et al. |
| 2013/0169957 | A1 | 7/2013 | Wolf et al. |
| 2013/0176552 | A1 | 7/2013 | Brown et al. |
| 2013/0264481 | A1* | 10/2013 | Chern ............ H01L 31/0216 250/358.1 |
| 2013/0270663 | A1 | 10/2013 | Lin et al. |
| 2013/0313440 | A1 | 11/2013 | Chuang et al. |
| 2013/0320211 | A1 | 12/2013 | Park et al. |
| 2013/0336574 | A1 | 12/2013 | Nasser-Ghodsi et al. |
| 2014/0034816 | A1 | 2/2014 | Chuang et al. |
| 2014/0111799 | A1 | 4/2014 | Lei et al. |
| 2014/0158864 | A1 | 6/2014 | Brown et al. |
| 2014/0203386 | A1 | 7/2014 | Bui |
| 2014/0204963 | A1 | 7/2014 | Chuang et al. |
| 2014/0246595 | A1 | 9/2014 | Menge |
| 2014/0291493 | A1 | 10/2014 | Chuang |
| 2014/0362203 | A1 | 12/2014 | Delaney |
| 2015/0177159 | A1 | 6/2015 | Brown et al. |
| 2015/0200216 | A1 | 7/2015 | Muramatsu et al. |
| 2015/0275393 | A1 | 10/2015 | Bondokov et al. |
| 2015/0294998 | A1 | 10/2015 | Nihtianov |

FOREIGN PATENT DOCUMENTS

| | | |
|---|---|---|
| EP | 1939917 A2 | 7/2008 |
| EP | 2346094 A1 | 7/2011 |
| JP | H0511287 A | 1/1993 |
| JP | 10171965 | 6/1998 |
| JP | 2003043533 A | 2/2003 |
| JP | 2004031452 A | 1/2004 |
| JP | 2007249092 A | 9/2007 |
| JP | 2007298932 A | 11/2007 |
| JP | 2009117454 A | 5/2009 |
| JP | 2010003755 | 1/2010 |
| KR | 100688497 | 3/2007 |
| KR | 100826407 | 5/2008 |
| RU | 2297070 | 4/2007 |
| WO | 9532518 A1 | 11/1995 |
| WO | 9617372 A1 | 6/1996 |
| WO | 2007-035858 A2 | 3/2007 |
| WO | 2011091159 | 7/2011 |
| WO | 2013006867 A1 | 1/2013 |
| WO | 2014067754 | 5/2014 |

OTHER PUBLICATIONS

Henderson, Brian S. "Study of Negative Electron Affinity GaAs Photocathodes", Department of Physics and Astronomy, Rice University, Houston, TX, Aug. 7, 2009, 18 pages.

Howorth, J. R. et al. "Transmission silicon photoemitters and electron multipliers," Journal of Physics D: Applied Physics, vol. 9, No. 5, Apr. 1, 1976, pp. 785-794.

Martinelli, Ramon U. "Infrared Photoemission from Silicon", Applied Physics Letters, vol. 16, No. 7, Apr. 1, 1970, pp. 261-262.

Martinelli, Ramon U. "Reflection and Transmission Secondary Emission from Silicon", Applied Physics Letters, vol. 17, No. 8, Oct. 15, 1970, pp. 313-314.

Sarubbi, Francesco et al. "Chemical Vapor Deposition of α-Boron Layers on Silicon for Controlled Nanometer-Deep p+n Junction Formation", Journal of Electronic Materials, vol. 39, No. 2, 2010, pp. 162-173.

Nikzad, Shouleh et al., Delta-doped CCDs: High QE with long-term stability at UV and visible wavelengths, SPIE vol. 2198 (1994), pp. 907-915.

Hecht, Eugene, Optics, 2nd Edition, Adelphi University, 1987, Addison-Wesley Publishing Co., Inc., 3 pages.

Hecht, Eugene, Optics, 4th Edition, India: Pearson Education Pte, Ltd. reprint 2004, 4 pages.

Tobin, Kenneth W. "Inspection in Semiconductor Manufacturing", Webster's Encyclopedia of Electrical and Electronic Engineering, Wiley & Sons, NY, 1999, vol. 10, pp. 242-262.

Nanver, Lis K. "Silicon Photodiodes for Low Penetration Depth Beams such as DUV/VUV/EUV Light and Low-Energy Electrons", Advances in Photodiodes,G. Betta, ed., Chapter 10, Mar. 22, 2011, pp. 205-224.

Nanver et al. "Pure-Boron Chemical-Vapor-Deposited Layers: a New Material for Silicon Device Processing", 18th IEEE International Conference on Advanced Thermal Processing of Semiconductors (RTP), Sep. 28, 2010-Oct. 1, 2010, pp. 136-139.

Sobieski, Stanley, "Intensified Charge Coupled Devices for Ultra Low Light Level Imaging", NASA, Goddard Space Flight Center, SPIE vol. 78 (1976) Low Light Level Devices, pp. 73-77.

Priority document U.S. Appl. No. 61/720,700, filed Oct. 21, 2012 corresponding to PCT/EP2013/071080 filed Oct. 9, 2013, pp. 1-44.

Fu et al. "Optimizing GaN photocathode structure for higher quantum efficiency", Optik, vol. 123, No. 9, May 2012, pp. 756-768.

Sarubbi F et al: "Pure boron-doped photodiodes: a solution for radiation detection in EUV lithography", Proceedings of the 38th European Solid-State Device Research Conference: Edinburgh International Conference Centre, Endiburgh, Scotland, UK, Sep. 15-19, 2008, Piscataway, NJ: IEE, US, Sep. 15, 2008, pp. 278-281.

KLA-Tencor Corporation; PCT International Search Report dated Dec. 8, 2015 for Application No. PCT/US2015/047307, 3 pages.

Huang, Qiyu et al., "Back-Side Illuminated Photogate CMOS Active Pixel Sensor Structure With Improved Short Wavelength Response", IEEE Sensors Journal, vol. 11, No. 9, Sep. 2011, 5 pages.

Itzler, Mark et al., "InP-based Geiger-mode avalanche photodiode arrays for three-dimensional imaging at 1.06 ∥m", Proceedings of SPIE, vol. 7320 (2000), 12 pages.

Niclass, Cristiano et al., "Design and Characterization of a CMOS 3-D Image Sensor Based on Single Photon Avalanche Diodes", IEEE Journal of Solid-State Circuits, vol. 40, No. 9, Sep. 2005, 8 pages.

Paetzel, Rainer et al., "Activation of Silicon Wafer by Excimer Laser" 18th IEEE Conf. Advanced Thermal processing of Semiconductors—RTP 2010, 5 pages.

Stevanovic, Nenad et al., "A CMOS Image Sensor for High-Speed Imaging", 2000 IEEE Int'l. Conference Solid-State Circuits, 3 pages.

Dulinski, Wojciech et al., "Tests of a backside illuminated monolithic CMOS pixel sensor in an HPD set-up", Nuclear Instruments and Methods in Physics Research A 546 (2005) 274-280, 7 pages.

Sarubbi, F et al, "Pure boron-doped photodiodes: a solution for radiation detection in EUV lithography", Proceedings of the 38th EP Solid-State Device Research Conf., Edinburgh Int'l Conf. Centre, Endiburgh, Scotland, UK, Sep. 15-19, 2008, Piscataway, NJ: IEEE, US, pp. 278-281.

Fu, Xiaoqian, "Higher Quantum Efficiency by Optimizing GaN Photocathode Structure", 978-1-4244-6644-3/10/ © 2010 IEEE, pp. 234-235.

KLA-Tencor Corporation; PCT International Search Report dated Dec. 29, 2015 for Application No. PCT/US2015/051538, 3 pages.

Sakic, Agata, "Boron-layer silicon photodiodes for high-efficiency low-energy electron detection", Solid-State Electronics 65-66 (2011), pp. 38-44.

Omatsu, Takashige et al., "High repetition rate Q-switching performance in transversely diode-pumped Nd doped mixed gadolinium yttrium vanadate bounce laser", Optics Express vol. 14, Issue 7, pp. 2727-2734, Apr. 3, 2006.

(56) References Cited

OTHER PUBLICATIONS

Utsumi, Vacuum Microelectrnoics: What's New and Exciting, IEEE vol. 38, No. 10, Oct. 1991, 8 pgs.
Armstrong, Carter M., The Quest for the Ultimate Vacuum Tube, Spectrum IEEE, Dec. 2015, 4 pgs.
Serbun, Pavel et al., Stable field emission of single B-doped . . . , JVSTB, 31, 02B101 (2013); doi: 10.1116/1.4765088, 7 pgs.
Sato, T. et al., Fabrication and characterization of HfC coated . . ., J. Vac. Sci. Technol. B 2194), published Jul. 31, 2003, 5 pgs.
NAGAO, Masayoshi, Fabrication of a Field Emitter Array with a Built-In Einzel Lens, JJAP 48 (2008) 06FK02, 4 pgs.
Rakhshandehroo, M.R., et al., Fabrication of a self-aligned silicon field emission . . . , JVSTB, 16, 765 (1998); doi: 10.1116/1,589900, 6 pgs.
Rakhshandehroo, M.R., et al., Field emission from gated Si emitter tips with precise . . . , JVSTB, 15, 2777 (1997); doi: 10.1116/1. 589726, 6 pgs.
Ding, Meng, Field Emission from Silicon, MIT 2001, 277 pgs.
Koike, Akifuni, Field Emitter Equipped With a Suppressor to Control Emission Angel, IEEE Electron Device Letters, vol. 34, No. 5, May 2013, 3 pgs.
Nagao, Masayoshi, Cathode Technologies for Field Emission Displays, IEJ Trans 2006; 1:171-178, 8 pgs.
Neo, Yoichiro, Electron Optical Properties of Microcolumn with Field Emitter, JJAP 52 (2013) 036603, 5 pgs.
Fowler, R.H. et al., Electron Emission in Intense Electric Fields, Mar. 31, 1928, 9 pgs.
Fanton, J. T., et al., "Multiparameter Measurements of Thin Films Using beam-profile reflectometry", Journal of Applied Physics, vol. 73, No. 11, p. 7035 (1993).
Unknown, Field Emitter Review, 7 pgs in Japanese.
Grubisic, D., et al., "New Silicon Reach-Through Avalanche Photodiodes with Enhanced Sensitivity in the DUV/UV Wavelength Range", MIPRO 2013, May 20-24, 2013, Opatija, Croatia, pp. 48-54.
Pain et al., "A Back-Illuminated Megapixel CMOS Image Sensor", Jun. 9, 2005, IEEE Workshop on Charge-Coupled Devices and Advanced Image Sensors, Karuizawa, Japan, 4 pgs.

\* cited by examiner

PHOTOCATHODE INCLUDING SILICON SUBSTRATE WITH BORON LAYER

RELATED APPLICATIONS

This application claims priority to U.S. Provisional Patent Application 61/679,200, entitled "Photocathode With Low Noise And High Quantum Efficiency, High Spatial Resolution Low-Noise Image Sensor And Inspection Systems Incorporating an Image Sensor" filed Aug. 3, 2012.

BACKGROUND OF THE INVENTION

Field of the Invention

The present invention generally relates to low light sensing detectors (sensors) used in conjunction with semiconductor wafer, reticle or photomask inspection systems, and more particularly to photocathodes utilized in the sensors for such inspection systems.

Description of the Related Art

Photocathodes are negatively charged electrodes typically used in light detection devices such as photomultipliers, image intensifiers and electron-bombarded CCDs (EBC-CDs). Photocathodes comprise a photosensitive compound that, when struck by a quantum of light (photon), generates one (or more) electrons in response to each absorbed photon due to the photoelectric effect. The photosensitive compound used in modern photocathodes typically comprises alkali metals because their low work-functions allow electrons to escape easily from the photocathode for detection by other structures of the host image sensor device. Compound semiconductors such GaAs and InGaAs are also used to make photocathodes, particularly for infra-red sensitive devices. Silicon photocathodes have been made in the past, but have not found significant commercial use because, although silicon is efficient at capturing light, few of the generated electrons are able to escape from the silicon, resulting in low overall efficiency.

Photocathodes are generally divided into two broad groups: transmission photocathodes and reflection photocathodes. A transmission photocathode is typically formed on the surface of a window (e.g., glass) that faces the source of light to be measured, and electrons exiting the photocathode pass through the photocathode's output surface for detection (i.e., the electrons move away from the light source). A reflective photocathode is typically formed on an opaque metal electrode base, where the light enters and the electrons exit from the same "illuminated" surface. Although reflection photocathodes simplify some of the tradeoffs between photocathode thickness and sensitivity that are discussed below, they are not suitable for use in imaging devices such as image intensifiers and EBCCD devices (although they can be suitable for use in some photomultiplier configurations). Therefore, in the discussion below, the term "photocathode" refers to transmission photocathodes only, unless otherwise specified.

Photocathodes are typically formed or mounted on a suitable host sensor's housing (e.g., a semiconductor or vacuum tube), and the sensor housing is positioned with the illuminated surface facing a target light source (i.e., such that the photocathode is positioned between the light source and the electron measuring structures of the host sensor. When photons are absorbed by a photocathode, on average about 50% of the generated electrons will travel towards the illuminated side of the photocathode (i.e., the side facing the light source through which the photons enter the photocathode). The other 50% of the photoelectrons will travel to the photocathode's output surface and, if the photoelectrons have sufficient energy, will be emitted toward the sensor's electron measuring structures. When an electron is emitted from the output surface of the photocathode, it will usually be accelerated by electric fields within the host sensor toward an anode, producing corresponding measurable voltages or currents that indicate the capture of one or more photons.

Photomultipliers are vacuum phototubes including a photocathode, an anode, and a series of dynodes (electrodes), where each dynode is at a successively more positive electrical potential than its predecessor, with the anode at a positive potential higher than that of the last dynode. A photoelectron emitted from the photocathode is accelerated by the photocathode-dynode electric field and will usually strike a dynode, which causes multiple secondary electrons to be emitted that are accelerated by the subsequent dynode-to-dynode electric field. Almost all of these secondary electrons will strike another dynode and generate yet more electrons. Eventually the electrons will arrive at the anode, usually after multiple stages of amplification by multiple dynodes. A photomultiplier therefore generates a pulse of current (i.e., a charge) every time a photon is absorbed and emits a photoelectron in the correct direction. Because the generated charge is equal to the charge on many electrons, when the gain is high enough it is possible to generate a charge that is above the noise level of the electronics. Photomultipliers can be therefore extremely sensitive detectors of light in the ultraviolet, visible, and near-infrared ranges of the electromagnetic spectrum. These detectors multiply the current produced by incident light by as much as 100 million times (i.e., 160 dB), in multiple dynode stages, enabling (for example) individual photons to be detected when the incident flux of light is very low.

An image intensifier is another type of vacuum tube sensor device that utilize a phosphor to increase the intensity of detected light in an optical system in order to facilitate, for example, visual imaging of low-light processes, or for conversion of non-visible light sources such as near-infrared or short wave infrared to visible. In typical image intensifiers, the photoelectrons emitted from a photocathode are accelerated toward a transparent anode coated with the phosphor such that the photoelectrons strike the phosphor with high energy (typically about 1 keV to about 20 keV), causing the phosphor to generate many photons. In some image intensifiers a microchannel plate is placed between the photocathode and phosphor in order to generate multiple secondary electrons from each photoelectron. Even without a microchannel plate, multiple photons can be generated at the output of an image intensifier for each absorbed photon. The emitted photons are directed by optics (such as a fiber optic bundle or lenses) to an image sensor. Since each absorbed photon can generate many output photons, very low light levels can be detected and measured, potentially even single photons under some conditions.

An EBCCD is another sensor operates in a similar manner to an image intensifier. Instead of a phosphor screen as the output, an image sensor such as a COD is used to detect the electrons that are emitted from a photocathode and accelerated by an electric field. In an EBCCD it is typical to use a potential difference of about −2 kV or more to generate the electric field between the photocathode and the CCD, whereby photoelectrons emitted by the photocathode are accelerated and strike the CCD with high energy, generating multiple electrons inside the CCD, which are then captured. Because multiple electrons are generated for each photon that is detected, the readout and dark noise of the CCD is less important than it would be for direct detection of photons. As compared with an image intensifier, the EBCCD avoids the cost of the optics needed to transfer the light from the phosphor to the image sensor, and also avoids the degradation in image resolution caused by those optics.

FIG. 11 shows a conventional EBCCD 50 comprising a housing 52 including a window 53, a photocathode 54 disposed on an inside surface of window 53, and a charge-coupled device (CCD) 55 disposed at a lower end of housing 52 such that photocathode 54 is separated from CCD 55 by a vacuum gap 56. An electric field is generated between the photocathode 54 and the CCD 55 by applying a voltage to the photocathode that is negative with respect to that of the CCD. An incoming photon 61 enters through window 53 and is absorbed by photocathode 54, causing a photoelectron to be generated. When a photoelectron 62 has sufficient energy to escape through the output side of photocathode 54 (i.e., downward in the figure), it enters gap region 56. Because CCD 55 is at a positive potential, usually of 2 kV or more, relative to photocathode 54, photoelectron 62 is accelerated towards CCD 55 such that it achieves an energy greater than about 2 keV, whereby photoelectrons will typically generate multiple electrons inside CCD 55. The electrons generated inside CCD 55 are then transmitted (e.g., by way of pins 57) to a processing system (not shown) that is configured to generate an associated image or other data associated with the detected photoelectrons.

Prior-art photocathodes require difficult tradeoffs between conflicting requirements associated with absorbing photons and emitting photoelectrons. A good photocathode needs to have a high probability of absorbing photons at wavelengths of interest, and a high probability of generating one (or more) photoelectrons from that absorbed photon. A good photocathode also needs to have a high probability that any photoelectron generated by an absorbed photon escapes from the photocathode. A thicker photocathode increases the probability that an incident photon will be absorbed, but also increases the probability that the resulting emitted photoelectron will recombine (i.e., be lost) before it escapes. More specifically, recombinations usually occur at defects or impurities in the material forming a photocathode, so the longer the distance the photoelectron must travel through the photocathode material, the greater the probability that it will encounter a defect or impurity and be recombined. The material must have a low work-function because only photoelectrons with energy close to, or greater than, the work-function have a reasonable probability of escaping.

Typically photocathodes are optimized for a relatively narrow range of wavelengths. For example, UV wavelengths are particularly useful in the semiconductor industry for detecting small particles and defects on semiconductor wafers because in general the amount of light scattered from a small particle depends, among other factors, on the ratio of the particle or defect size to the wavelength. Most photocathode materials absorb UV light strongly. A prior-art photocathode optimized for UV wavelengths usually needs to be thin because UV photons will be absorbed close to the illuminated surface. If the photocathode is not thin, the photoelectron may have a low probability of escaping from the output surface of the photocathode. Typically only photoelectrons that escape on the side of the photocathode facing the phosphor or image detector will generate an output signal. Such a thin photocathode optimized for UV wavelengths will typically have poor sensitivity at visible and infra-red wavelengths as a significant fraction of the incident photons at longer wavelengths will pass through the photocathode without absorption.

Another limitation of prior-art photocathodes is that the energy of the emitted photoelectron varies with the wavelength of absorbed light and may be several eV when a UV photon is absorbed. Because the direction in which the photoelectron is emitted is random, this electron energy results in a spread of the signal in a horizontal direction. Furthermore, the spread will vary with the wavelength of the absorbed photon, being greater for shorter wavelengths. In a thick photocathode, a photoelectron will usually undergo multiple collisions before being emitted and will be more likely to have an energy that is close to that determined by the temperature of the photocathode (i.e., the electron is more likely to be thermalized). However, when an electron undergoes multiple collisions within a photocathode, it is likely to recombine and be lost due to the high level of defects within and/or on the surface of prior-art photocathode materials. Hence, a reduced energy spread would come at the cost of substantially reduced sensitivity (most incident photons would no longer produce a signal).

Single-crystal (monocrystalline) silicon would appear to overcome many of the disadvantages just described. Silicon absorbs all wavelengths shorter than about 1.1 µm. Silicon crystals can be grown with very high purity and very few crystal defects. The recombination lifetime of electrons in high-quality single crystal silicon can be many microseconds, even hundreds of microseconds in the best quality material. Such long recombination lifetimes allow electrons generated many microns away from the surface to be able to migrate to a surface with a low probability of recombining.

However, in spite of its many advantages, the development of silicon-based photocathodes for commercial use has been prevented by two main disadvantages.

One disadvantage of silicon is that silicon has a relatively large work-function (approximately 4.8 eV, Allen and Gobelli, "Work Function, Photoelectric Threshold, and Surface States of Atomically Clean Silicon", Physical Review vol. 127 issue 1, 1962, pages 150-158) that works against the emission of photoelectrons generated by the absorption of photons. A material's work-function is the energy difference between an electron at the Fermi level and one at the vacuum level (i.e. that has escaped from the material). Silicon's relatively large band gap means that thermalized electrons cannot escape from silicon. Even UV photons absorbed close to the surface of silicon do not create much photocurrent because the photoelectrons do not have enough energy to escape. For example, a photon energy of 6.5 eV creates a photoelectron with an energy of about 3 eV (because direct absorption is more likely than indirect absorption at such a wavelength). A photoelectron with an energy of about 3 eV is not able to escape from the silicon because of the silicon work-function.

A second, more serious, problem with the use of silicon as a photocathode material is that silicon very readily forms a native oxide on its surface. Even in a vacuum, a native oxide will eventually form as the small amounts of oxygen and water present in the vacuum will react with the surface of the silicon. The interface between silicon and silicon dioxide has defects (due to dangling bonds) where the probability of an electron recombining is very high. Furthermore, the band gap of silicon dioxide is large (about 8 eV) creating an additional barrier higher than the work-function that an electron has to overcome in order to escape, even if the oxide is very thin (native oxide on a very smooth silicon surface is typically about 2 nm thick). The defect density at the silicon to oxide interface can be reduced by removing the native oxide and growing a thermal oxide at high temperature such as approximately 900-1000° C. Such a layer can be stable when grown to a thickness of about 1.5 nm to 2 nm.

However, even a good quality thermal oxide has a significant defect density at its interface to silicon (typically $10^9$ to $10^{11}$ defects per $cm^2$), and the high band gap of the oxide combined with a minimum thickness of close to 2 nm still provides a significant barrier to electrons escaping even if the work-function can be overcome. A thin silicon nitride layer can be used to prevent growth of a native oxide layer on silicon, but the density of defects is higher at the silicon to silicon nitride interface than at the silicon to silicon dioxide interface, and the band gap for silicon nitride (about 5 eV) is large enough to prevent most electrons from escaping from the surface. For these reasons, silicon has never found significant commercial use as a photocathode.

What is therefore needed is a photocathode that overcomes some, or all, of the limitations of the prior art.

SUMMARY OF THE INVENTION

The present invention is directed to a photocathode structure including a silicon substrate, a boron (first) layer formed on at least the output surface of the silicon substrate, and a low work function (second) layer formed on the boron layer. The silicon substrate is preferably essentially defect-free monocrystalline (single-crystal) silicon having a thickness in the range of about 10 nm to about 100 µm, where the thickness depends in part on the wavelength of light to be captured. The boron layer is preferably formed using a high temperature deposition process (e.g., between about 600° C. and 800° C.) on clean, smooth silicon in a manner that produces a pin-hole free boron layer having a thickness in the range of 1-5 nm (preferably about 2 nm), whereby the boron layer circumvents silicon's oxidation problem by reliably sealing the silicon surface against oxidation. A low work-function material (e.g., either an alkali metal such as cesium or an alkali metal oxide such as cesium oxide) is then deposited on the boron layer to enable electron emission from the silicon substrate, whereby the low work-function material layer circumvents silicon's relatively high work function problem by effectively creating a negative electron affinity device. Thus, by producing a photocathode having both a smooth boron layer and a low work-function material layer formed on the single-crystal silicon substrate, the present invention provides the beneficial qualities of silicon (i.e., sub-1 µm wavelength absorption, high purity/low defect material, and long electron recombination times), while avoiding the negative aspects that have previously prevented the widespread commercial use of silicon-based photocathodes.

According to various alternative embodiments of the present invention, various additional layers and structures are utilized to further enhance the beneficial qualities of the inventive photocathode structure. In some embodiments, a second boron layer (third layer) is formed on the illuminated (first) surface of the silicon substrate to further prevent oxides and defects that can reduce photon absorption, and an anti-reflective material layer (fourth layer) is disposed on the third layer to further enhance photon absorption. In some embodiments, a metal frame or grid and a voltage source are utilized to generate an external potential difference between the illuminated and output surfaces of the silicon substrate in order to cause electrons to preferentially move towards the output surface. In yet other embodiments, boron (or another p-type dopant) is diffused into the silicon substrate through the illuminated surface to form a p-type dopant region to create a potential gradient that drives electrons away from the illuminated silicon surface where they might recombine and be lost.

In accordance with alternative specific embodiments, the inventive photocathode structures of the present invention are incorporated into various sensor structures to provide sensors exhibiting superior low light sensing capability. In addition to the photocathode (which is positioned adjacent to a receiving surface of the sensor), these sensor structures include a detection device (e.g., a CCD or CMOS image sensor) having a detecting surface that faces the output surface of the photodiode and is spaced from the low work-function material layer by an intervening gap, where the detection device serves to detect photoelectrons emitted through the output surface of the photocathode, and to generate electric signals indicating the capture of photoelectrons. In some sensor embodiments, the sensor structure is an electron-bombarded charge-coupled device (EBCCD) that may (or may not) have a window on top of the photocathode. In other embodiments of the invention, the sensor is an image intensifier that may (or may not) have a window on top of the photocathode. In yet other embodiments of the invention, the sensor is a photomultiplier that may (or may not) have a window on top of the photocathode.

In some sensor embodiments, a second boron layer is formed on the illuminated surface of the photocathode to prevent oxide formation on the illuminated surface, and an anti-reflective material layer is provided over the second boron layer to improve photon capture efficiency. In some of these embodiments, the anti-reflective material layer is disposed between a window and the photocathode, but in other embodiments the anti-reflective material layer also serves as the sensor's receiving surface (i.e., the sensor does not have a window over the illuminated surface of the photocathode), which further increases photon capture efficiency by the sensor. In other sensor embodiments that include a window over the illuminated surface of the photocathode, an anti-reflective material layer is provided on the window to improve photon capture efficiency.

In some embodiments of the invention, a sensor including the photocathode of the present invention also includes a silicon-based detection device having an additional boron layer on its receiving surface (i.e., the surface of the detection device facing the photocathode). For example, in cases where the sensor is an electron-bombarded CCD (EBCCD) and the detection device is a CCD (which are typically formed on silicon substrates), a boron layer is formed directly on the COD's receiving surface during fabrication to improve electron capturing efficiency of the sensor by preventing the formation of a silicon dioxide layer on the COD's receiving surface. In other embodiments, the sensor includes a CMOS detector (i.e., instead of a CCD), and the additional boron layer is formed on the receiving surface of the CMOS detector.

In other embodiments of the invention, sensors including the inventive photocathode are utilized in wafer, reticle or photomask inspection systems. In particular, the inventive systems include an illumination source (e.g., a laser system) for transmitting light onto a sample/wafer, one or more sensors (e.g., a photomultiplier, an image intensifier or an EBCCD) that utilize any of the inventive photocathodes described herein to detect photons passing through or reflected by the sample/wafer, and an associated optical system for guiding the light/photons from the illumination source to the sample (wafer, reticle or photomask), and from the sample to the sensor.

BRIEF DESCRIPTION OF THE DRAWINGS

The present invention is illustrated by way of example, and not by way of limitation, in the figures of the accompanying drawings in which.

DETAILED DESCRIPTION

The present invention relates to an improvement in low light sensors for semiconductor inspection systems. The following description is presented to enable one of ordinary skill in the art to make and use the invention as provided in the context of a particular application and its requirements. As used herein, directional terms such as "top", "bottom", "over", "under", "upper", "upward", "lower", "down" and "downward" are intended to provide relative positions for purposes of description, and are not intended to designate an absolute frame of reference. Various modifications to the preferred embodiment will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

Figure 1:
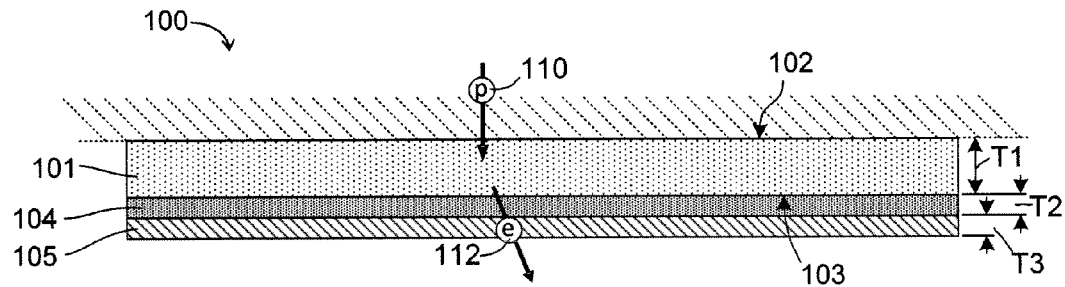
FIG. 1 is a cross-sectional side view illustrating a photocathode formed on a silicon substrate according to a simplified embodiment of the present invention.

FIG. 1 illustrates, in cross section view, a photocathode 100 according to a generalized embodiment of the present invention. Photocathode 100 generally includes a silicon substrate 101 having an upward-facing illuminated (top/first) surface 102 and an opposing downward-facing output (bottom/second) surface 103, a boron (first) layer 104 disposed at least on output surface 103, and a low work-function (second) layer 105 disposed on a lower surface of boron layer 104. Photocathode 100 operates similar to conventional photocathodes in that, when positioned properly, photons 110 entering silicon substrate 101 through illuminated (upper) surface 102 are absorbed and create photoelectrons 112 that are often emitted from substrate 101 through output surface 103. Note that FIG. 1 shows a dashed-line structure covering illuminated surface 102 to indicate the optional presence of a window and/or protective and/or antireflection coatings on illuminated surface 102, some of which are addressed in the various specific embodiments discussed below.

According to an aspect of the present invention, silicon substrate 101 preferably comprises monocrystalline silicon (i.e., a single crystal of silicon) that is p-type doped with a doping level less than about $10^{19}$ cm$^{-3}$, i.e. a resistivity of about 0.005Ω cm or higher. Since minority carrier lifetime and diffusion length decrease with increasing dopant concentration, dopant concentrations higher than about $10^{19}$ cm$^{-3}$ may be used when the silicon is very thin, such as thinner than about 1 μm, whereas when the silicon is thicker than about 1 μm, dopant concentrations lower than about $10^{19}$ cm$^{-3}$ may be preferred. In other embodiments, silicon substrate 101 comprises polycrystalline silicon or multi-crystalline silicon. Depending on the intended wavelength operating range of the photocathode, the silicon may be between about 10 nm and about 100 μm in thickness. Silicon substrate 101 exhibits a band gap of approximately 1.1 eV, so light with a vacuum wavelength shorter than approximately 1.1 μm is absorbed. The 1.1 eV band gap of silicon substrate 101 is indirect, so absorption of wavelengths in the red and infra-red part of the spectrum is weak. Silicon substrate 101 also has a direct band gap of approximately 3.5 eV, so it strongly absorbs deep UV wavelengths. Depending on the intended use for photocathode 100, silicon substrate 101 has a thickness T1 in the range of approximately 20 nm to approximately 100 μm. For example, in order to facilitate a high probability of absorbing a photon in the infra-red part of the spectrum, silicon substrate 101 is formed with a thickness T1 of about 10 μm or several tens of μm. Alternatively, for absorbing UV wavelengths, silicon substrate 101 is formed with a thickness T1 in a range of a few tens of nm to about 100 nm. In a practical embodiment, silicon substrate 101 has a thickness T1 of about 1 μm in order to absorb at least 85% of the unreflected incident photons over a wavelength range from the vacuum UV to approximately 670 nm near the red end of the visible spectrum. When silicon substrate 101 comprises a monocrystalline (single crystal) structure that is grown with very low density of crystal defects and high purity using known techniques, a photoelectron generated inside silicon substrate 101 has a potential lifetime of tens or hundreds of microseconds (μs). In addition, the single crystal structure causes photoelectrons to lose much of their excess energy and partially, or substantially, thermalize with a low probability of recombining.

According to another aspect of the present invention, boron layer 104 comprises essentially pure boron that is disposed directly on output surface 103 of the silicon substrate 101. As used herein, the phrase "directly on" in conjunction with the boron-to-silicon interface is intended to mean that there are no continuous intervening layers (e.g., oxide or SiN$_x$ layers) separating output surface 103 and boron layer 104 other than a possible thin layer (i.e., a few monolayers) of SiB$_x$ that may form at the Si/B interface. Note also that the phrase "directly on" does not preclude the presence of oxide between some portions of the boron and silicon. Boron layer 104 is grown on clean smooth silicon a high temperature (i.e., at a temperature higher than approximately 500° C., preferably between about 600° C. and 800° C.) using techniques taught by F. Sarubbi et al. "Chemical Vapor Deposition of α-Boron Layers on Silicon for Controlled Nanometer-Deep p+n Junction Formation", Journal of Electronic Materials, Vol. 39, No. 2, (February 2010) pp. 162-173, ISSN 0361-5235 such that the boron forms a pin-hole free coating having a thickness T2 in the range of approximately 1 nm to 5 nm, preferably approximately 2 to 3 nm. As Sarubbi et al. explain on p 163 of the cited reference, it is important to remove all native oxide from the silicon by, for example, a wet clean followed by an in-situ thermal clean prior to depositing the boron. Lower temperature deposition of boron is also possible, though the coating may be less uniform, and a coating thicker than 2 nm may be needed to ensure that it is pin-hole free. An advantage of boron layer 104 is that such a pin-hole free coating, when applied to a clean silicon surface, prevents formation of a native oxide on output surface 103. An advantage of providing boron layer 104 between silicon substrate 101 and low work function material layer 105 (e.g., alkali metal or alkali metal oxide) is that the boron prevents a silicon dioxide layer from forming between the low work function material and the silicon. As previously described, a silicon dioxide layer has a high band gap and even thin layers can block a significant fraction of electrons from leaving the silicon. The boron layer thus allows even electrons with low energies to leave the silicon and enter the alkali metal or alkali metal oxide layer. Although it is known in the art to coat a silicon photocathode with a low work-function material such as cesium oxide, prior art devices could not avoid a silicon dioxide interface layer from forming between the silicon and the low work-function material, even if the silicon layer was free of oxide when coated. That is, without an impervious pin-hole-free protection layer on the silicon, oxygen eventually migrates to the silicon surface and forms an oxide layer. An advantage of forming layer 104 using boron is that even a thin pin-hole-free boron layer is impervious to oxygen and protects the silicon. Another advantage of the boron coating is that the density of defects and interface traps at the silicon to boron interface is typically lower than at the silicon to silicon dioxide interface.

According to another aspect of the present invention, low work function material layer 105 is provided to lower the work-function at output surface 103 by creating a negative electron affinity device at output surface 103. In one embodiment, low work function material layer 105 comprises at least one of alkali metals or alkali metal oxides, which have a low work-function that allows electrons to readily escape silicon substrate 101. In embodiments of this invention alkali metals or alkali metal oxides are coated on top of boron layer 104 (i.e., on the output side of photocathode 100). In some embodiments that alkali metal or alkali metal oxide is cesium or cesium oxide. In other embodiments other alkali metals, other alkali metal oxides, mixtures of different alkali metals or alkali metal oxides are used. In some embodiments other elements are added to the alkali metal(s) or alkali metal oxide(s). In preferred embodiments, the alkali metal or alkali metal oxide layer 105 has a thickness T3 that is less than about 2 nm thick. In some embodiments, layer 105 is less than about 1 nm thick. Cesium and cesium oxide layers have been used to create negative electron affinity surfaces on semiconductor photocathodes for many decades. A recent description can be found in the report entitled "Study of Negative Electron Affinity GaAs Photocathodes", by B. S. Henderson, dated Aug. 7, 2009.

Figure 2A:
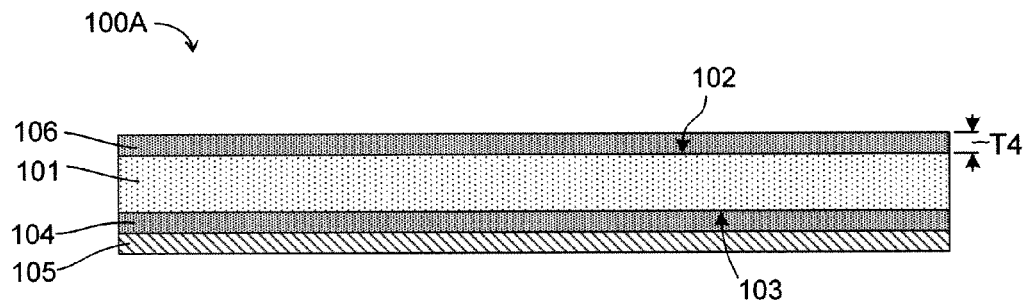
FIGS. 2(A), 2(B) and 2(C) are cross-sectional side views illustrating silicon photocathodes according to alternative specific embodiments of the present invention.
Figure 2B:
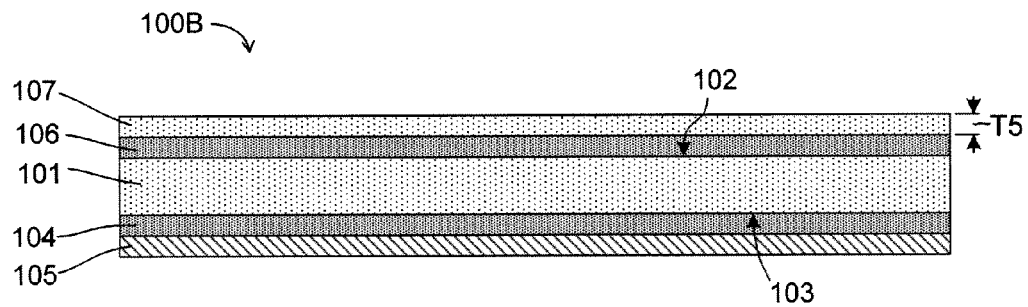
Figure 2C:
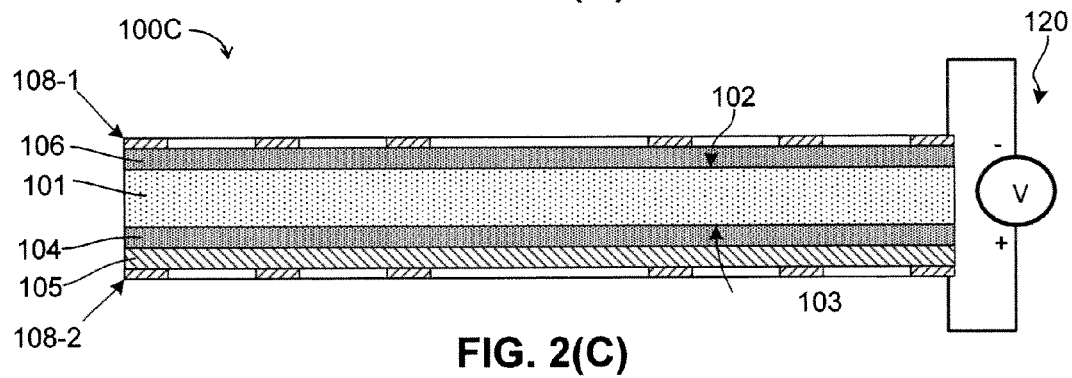

FIGS. 2(A) to 2(C) illustrate inventive photocathodes according to various alternative embodiments of the present invention in which additional layers and structures are utilized to further enhance the beneficial qualities of the inventive photocathode structure. The illustrated exemplary embodiments are not intended to be exhaustive, and photocathodes including combinations of the additional layers and structures described below are understood to be possible.

FIG. 2(A) illustrates, in cross section view, a photocathode 100A according to a first alternative embodiment. Similar to the structure described above, photocathode 100A includes a silicon substrate 101 having a boron layer 104 disposed on output surface 103, and a low work-function layer 105 disposed on boron layer 104. In addition, photocathode 100A includes a second boron layer (third layer) 106 that is formed on upward-facing illuminated (first) surface 102 of silicon substrate 101 using the techniques described above with reference to the formation of boron layer 104. Although boron does absorb at UV wavelengths, by forming a second boron layer 106 with a thickness T4 of approximately 3 nm or less, only a small fraction of the incident photons are absorbed. Furthermore, since boron is a p-type dopant in silicon, the presence of a boron coating will tend to drive photo-electrons away from illuminated surface 102. This improves the efficiency of photocathode 100A by reducing the likelihood of electrons recombining at illuminated surface 102. A similar result can be achieved by implanting a p-type dopant in a very shallow layer at the surface, as discussed below with reference to FIG. 3. In other embodiments of the present invention (not shown), illuminated surface 102 is not protected by a boron layer, but instead boron (or another p-type dopant) is implanted (diffused) into the silicon below illuminated surface 102. The presence of an oxide coating on the illuminated surface need not significantly degrade the quantum efficiency and, with the appropriate choice of oxide thickness, can usefully reduce the reflectivity of the silicon at a wavelength of interest.

FIG. 2(B) illustrates, in cross section view, a photocathode 100B according to a second alternative embodiment including a silicon substrate 101, a lower boron layer 104 disposed on output surface 103, a low work-function layer 105 disposed on boron layer 104, and an upper boron layer 106 disposed on illuminated surface 102. Photocathode 100B differs from the previously discussed embodiments in that it further includes one or more anti-reflection coating layers (fourth layer) 107 disposed on upper boron layer 106. Anti-reflection coating layer 107 is formed using materials that are useful for UV and deep UV anti-reflection layer, including (but not limited to) silicon dioxide, silicon nitride, magnesium fluoride, and hafnium dioxide. For photocathodes that need high quantum efficiency at UV wavelengths, the density of defects and trapped charges at and near illuminated surface 102 must be kept low because UV photons are absorbed near illuminated surface 102. As mentioned above, any dielectric material coated directly on the surface of silicon substrate 101 will create defects and trapped charges at the surface and within the bulk of the dielectric, and will degrade the quantum efficiency of the photocathode particularly for deep UV wavelengths that are absorbed close to the surface. By first forming upper boron layer 106 as a thin pin-hole-free layer (e.g., approximately 2 nm to 5 nm), illuminated surface 102 remains essentially free of defects and trapped charges, and photocathode 100B includes enhanced high quantum efficiency that is provided by anti-reflection coating layer 107. Upper boron layer 106 can also, at least partially, shield silicon substrate 101 from trapped charges in any additional layers disposed over anti-reflection coating layer 107.

FIG. 2(C) illustrates a photocathode 100C according to a third alternative embodiment including silicon substrate 101, lower boron layer 104 disposed on output surface 103, low work-function layer 105 disposed on boron layer 104, and upper boron layer 106 disposed on illuminated surface 102. Photocathode 100C differs from the previous embodiments in that an external voltage source 120 is connected to generate an external potential difference between illuminated surface 102 and output surface 103 in order to cause electrons generated in silicon substrate 101 to preferentially move towards output surface 103. In this embodiment, output surface 103 is held at a positive potential relative to illuminated surface 102. Because the highly doped silicon forming substrate 101 is a weak conductor, generating a suitable potential difference (e.g., less than approximately 5 V) between illuminated surface 102 and output surface 103 serves to generate a higher flow of photoelectrons through output surface 103. In some embodiments, metal borders around the edges of the photocathode (not shown) or sparse metal grids 108-1 and 108-2 are respectively formed on upper boron layer 106 and low work-function layer 105 to ensure a good electrical connection to the opposing surfaces of photocathode 100C.

Figure 3:
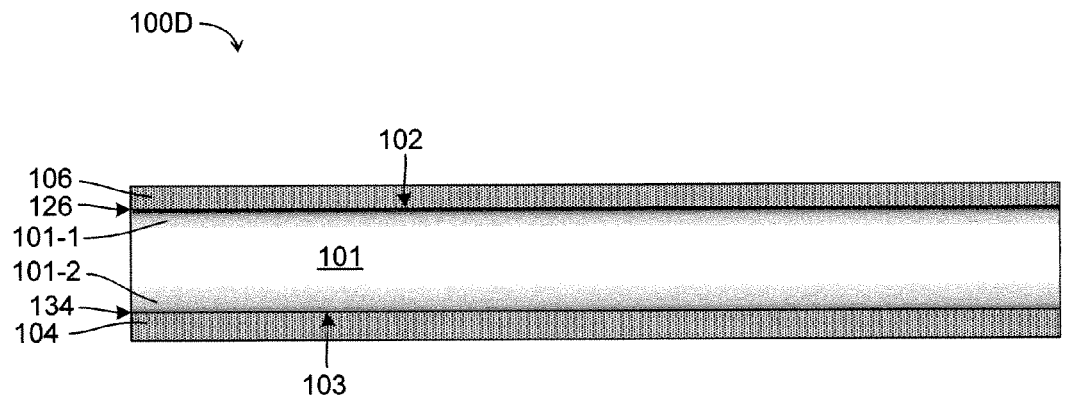
FIG. 3 is an enlarged partial cross-sectional side view illustrating doping and additional structures formed on the silicon substrate of a photocathode formed in accordance with another exemplary embodiment of the present invention.

FIG. 3 shows a cross-section view of a photocathode 100D according to another embodiment of the present invention in which gradients of dopants are purposefully diffused into substrate 101 from one or both of illuminated surface 102 and output surface 103 to direct photoelectrons within the silicon towards output surface 103. The low work function material layer is omitted for brevity. In the illustrated embodiment (i.e., where illuminated surface 103 is coated with upper boron layer 106), a thin boron silicide layer 126 is formed between the silicon and boron. Some of the boron will diffuse into silicon to form diffusion region 101-1 (indicated by shaded area), thereby creating a potential gradient that will tend to drive electrons away from illuminated surface 102 into substrate 101. In those embodiments of the invention with no boron coating on the illuminated surface, a p-type dopant, such as boron, is implanted or diffused into the silicon from the illuminated surface in order to create diffusion region 101-1. Similarly, on output surface 103, a very thin (one, or a few, monolayers) boron silicide layer 134 is formed between silicon substrate 101 and boron layer 104, and some of the boron will diffuse a short distance into the silicon to form a diffusion region 101-1 (indicated by shading). In some embodiments, the diffusion layer 101-2 may comprise other p-type or n-type dopants implanted into the silicon in order to modify the electric field gradients near output surface 103.

Figure 4:
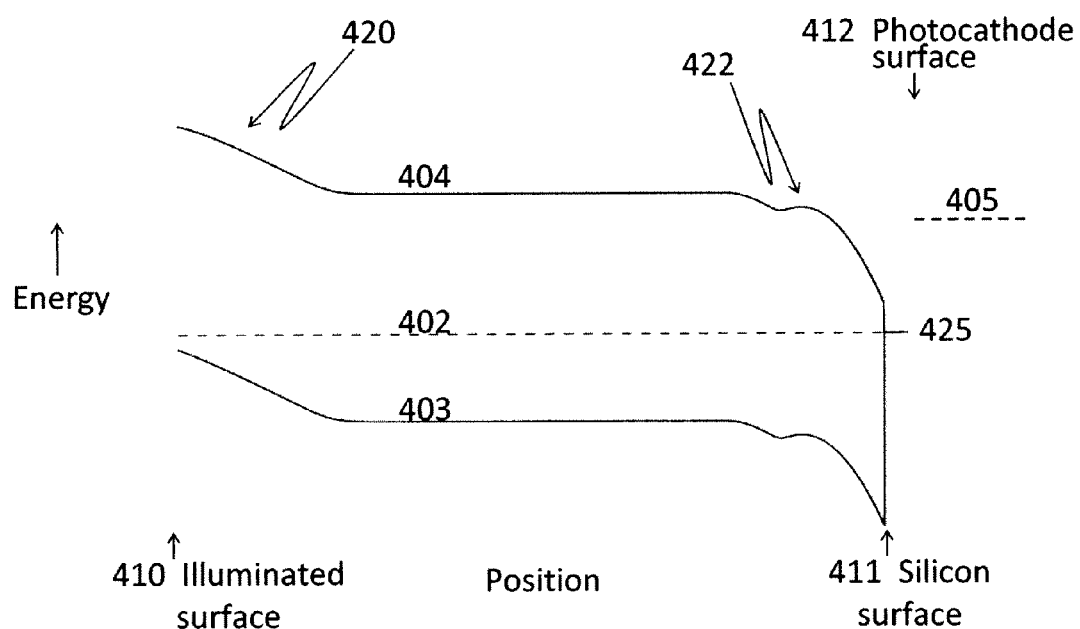
FIG. 4 is an energy diagram illustrating exemplary electron energy levels inside the silicon substrate of a photocathode formed in accordance with the present invention.

FIG. 4 is a diagram illustrating exemplary energy levels as a function of electron position within a cross section of an exemplary inventive photocathode formed in accordance with the embodiments described above. The vertical direction represents energy. Note that this figure is not to scale, is distorted and some aspects are exaggerated in order to more clearly illustrate key aspects of the photocathode. The illuminated (top) surface of the photocathode 410 is shown on the left, and the output (bottom) surface 412 is shown on the right. Dashed line 402 represents the Fermi level within the photocathode when no external voltage is applied to the photocathode. When no external voltage is applied, the Fermi level is essentially the same everywhere within the photocathode.

Line 403 represents the top of the valence band within the semiconductor. The illuminated surface 410 of the photocathode is heavily p doped, either from explicit doping or from diffusion of boron from a surface boron coating (not shown because, if present, it is only a few nm thick), or from a combination of the two. Because of the heavy p-type doping near the surface, the Fermi level is just above the top of the valence band. For example, for high levels of boron doping, the gap between the Fermi level and the top of the valence band might be as small as approximately 0.045 eV. As the dopant concentration decreases away from the surface, the gap between the Fermi level and the top of the valence band increases causing the conduction and valence bands to bend down away from the surface as indicated by arrow 420.

Line 404 represents the bottom of the conduction band. The difference between the bottom of the conduction band and the top of the valence band is called the band gap. For silicon the band gap is approximately 1.1 eV, but reduces where the dopant concentration is high. When a free electron is created by absorption of a photon, that electron will be in the conduction band. The electron is initially created with an energy that is approximately equal to the difference between the photon energy and the band gap. In silicon, the excess energy is usually quickly lost, so that the electron quickly reaches an energy close to the bottom of the conduction band. Because of the downward slope indicated by arrow 420 in the conduction band is close to the illuminated surface, any electrons created near that surface will quickly move away from that surface and are unlikely to recombine at any defects that exist on or near the illuminated silicon surface 410. Since deep UV photons are very likely to be absorbed within a few nm of the illuminated silicon surface 410, high quantum efficiency of the photocathode at deep UV wavelengths is made possible by this dopant profile near the surface.

The second surface 412 of the photocathode is coated with a low-work-function material as described above on top of a thin boron layer that is directly on the silicon. Since the low-work-function material is conducting, its Fermi level is within its conduction band. This is shown by solid line 425 as the merging of the Fermi level and the conduction band. Since both the boron layer and the low-work-function layer are just a few nm thick, they are shown as one combined conductive layer. As explained above, some of the boron diffuses into the silicon creating p-type silicon near the surface. In some embodiments additional dopants may be incorporated into the silicon. Electrons can lower their energy by moving from the low-work-function material into the p-type doped silicon. This creates a positive charge on the surface 412. That positive charge causes the conduction and valence bands to curve down as shown as 422. The shape of the slopes in the conduction and valence bands at 422 may not be monotonic because there is both a dopant concentration profile away from the silicon surface 411 into the silicon and a depletion region created by migration of electrons from the low-work-function material into the silicon. Depending on the exact shape of the dopant concentration profile, there may be a small local minimum or maximum in the energy curves of the conduction and valence bands near the surface. Such small deviations from a monotonic shape do not significantly impact the performance of the device if their heights are no more than a few tenths of an eV and/or the widths of any maxima are no more than a few nm.

Dashed line 405 represents the vacuum energy level. The difference between 405 and 425 represents the work function of the low-work-function material on the photocathode surface 412. In some preferred embodiments, the work function of the low-work-function material is low enough that the vacuum level 405 is below the energy level of the substantially flat region of the conduction band within the silicon. This results in what is known as a negative electron affinity device. Electrons in the conduction band of the silicon can easily escape from the surface 412 resulting in an efficient photocathodes. Even if the vacuum level 405 is a few tenths of an eV above the substantially flat region of the conduction band within the silicon, the probability of an electron escaping can still be very high. If the vacuum level 405 is above the substantially flat region of the conduction band within the silicon, electrons can readily escape from the surface 412 if the surface 412 is made slightly positive relative to the surface 410.

Applying a positive voltage to surface 412 relative to surface 410 makes the Fermi level slope down from left to right, causing similar slopes to be added to the intrinsic slopes in the conduction and valence bands. This will accelerate electrons as the move from surface 410 towards surface 412 and allow them to reach surface 412 with enough energy to have a high probability of escaping.

In prior art photocathodes based on silicon, there would be a thin oxide layer on the surface 411 of the silicon. This oxide, even though only about 2 nm thick, represents a substantial barrier to any electrons trying to escape. The band gap of silicon dioxide is approximately 8 eV. Such a large band gap results in a local peak in the conduction band that is several eV higher than the conduction band within the silicon. The boron layer on the surface 411 blocks oxygen or water from reaching the silicon surface and prevents growth of an oxide layer, thus enabling an efficient photocathode.

Figure 5A:
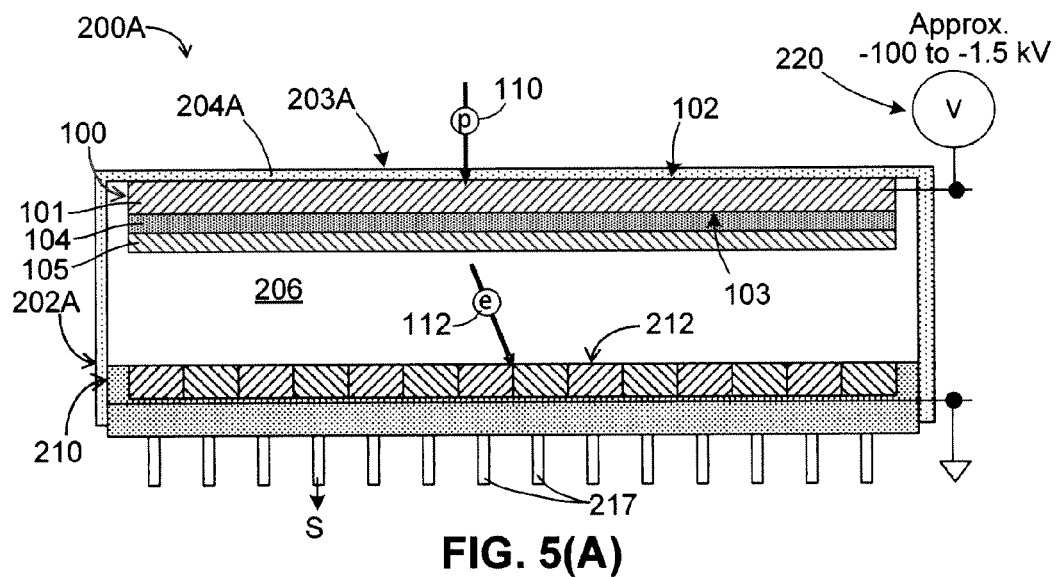
FIGS. 5(A), 5(B) and 5(C) are cross-sectional side views illustrating exemplary sensors including the photocathode according to alternative specific embodiments of the present invention.
Figure 5B:
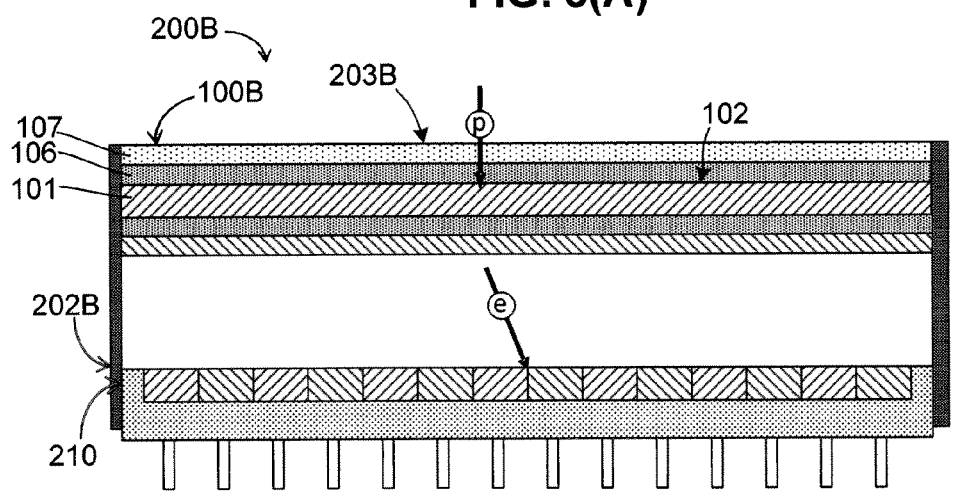
Figure 5C:
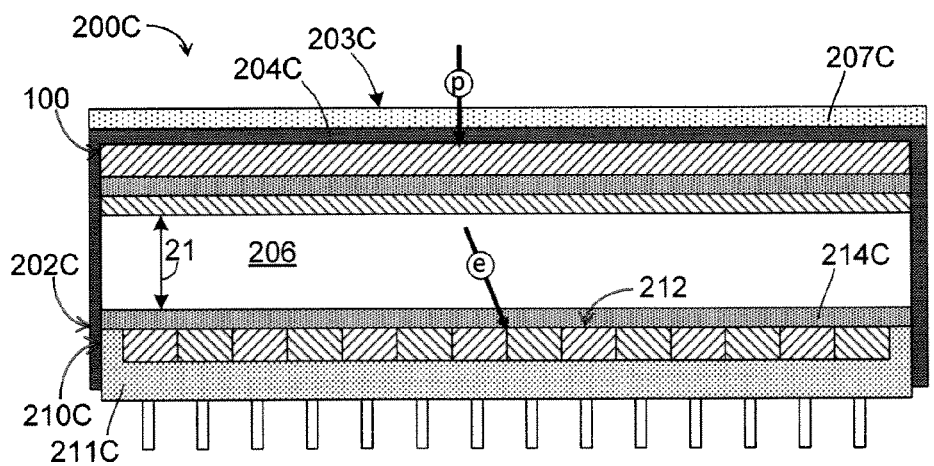

FIGS. 5(A) to 5(C) are simplified cross-sectional figures showing various sensor structures accordance with alternative specific embodiments, where each of the sensor embodiments includes an inventive photocathode structure according to at least one of the embodiments set forth above, thereby providing sensors having superior low light sensing capability that can be utilized, for example, in semiconductor inspection systems. Although the simplified sensor structures shown in FIGS. 5(A) to 5(C) are consistent with EBCCD-type sensors, it is understood that the depicted sensor structures are applicable to other sensor structures as well (e.g., image intensifier and photomultiplier sensors).

FIG. 5(A) illustrates in cross section a sensor 200A in accordance with a first sensor embodiment of the present invention. Sensor 200A generally includes silicon photocathode 100, which is described above, a detection device 210 (e.g., a CCD or CMOS image sensor), and a housing 202A operably connected between photocathode 100 and detection device 210 such that a detecting surface 212 of detection device 210 is separated from the low work-function material (second) layer 105 of photocathode 100 by an intervening gap region 206. Photocathode 100 is disposed adjacent to a receiving surface 203A of sensor 200A and arranged such that an illuminated surface 102 faces away from detection device 210, thereby orienting photocathode 100 to receive radiation (e.g., photons 110) and to emit photoelectrons 112 across intervening gap region 206 to detection device 210. As set forth above with reference to FIG. 1, photocathode 100 is characterized by having a boron (first) layer 104 formed on output (second) surface 103 of a (e.g., monocrystalline) silicon substrate 101, and low work function material layer 105 disposed on boron layer 104. Similar to most CCD and CMOS image sensor devices, detection device 210 includes sensing structures for detecting photoelectrons 112 and circuitry for generating an electric signal S (e.g., by way of one or more output pins 217) in response to the detected photoelectrons.

According to an aspect of the illustrated embodiment, photocathode 100 is bonded or otherwise hermetically sealed to a non-conducting or highly resistive glass or ceramic window 204A that, in conjunction with side wall and other portions of housing 202A, for an envelope whose interior is evacuated (i.e., gap region 206 is essentially filled with a vacuum). In one specific embodiment, the bond between window 204A and photocathode 100 is formed by a silicon dioxide layer disposed around the edge of photocathode 100. In some embodiments, silicon substrate 101 of photocathode 100 may be a few tens of microns to a few hundred microns thick. Such thicknesses are strong enough to withstand the force of atmospheric pressure from the outside without any window on top of photocathode. Materials suitable for use in forming window 204A include fused silica, quartz, alumina (sapphire), magnesium fluoride and calcium fluoride.

According to another aspect of the first sensor embodiment, sensor 200 includes conductive structures (e.g., similar to the grid structure described above with reference to FIG. 2(C)) that are operably disposed on or adjacent to photocathode 100 and detection device 210 such that, when a suitable voltage supply 220 is operably coupled to sensor 200A, an electric field is generated between photocathode 100 and detection device 210 that serves to accelerate electrons 112 emitted from photocathode into gap region 206 toward detection device 210. In some embodiments, as explained above with reference to FIG. 2(C), output surface 103 of photocathode 100 is held at a potential of less than about 5 V positive relative to the illumination surface 102 by a second voltage source (not shown). Electrons are emitted by the photocathode 100 when radiation (photons) 110 is absorbed, and electrons 112 emitted into gap region 206 are accelerated towards detection device 210 because the photocathode 100 is held at a negative potential relative to detection device 210 by voltage source 220. In preferred embodiments the potential difference generated by voltage source 220 is in a range of approximately 100 V to approximately 1500 V.

FIG. 5(B) shows a sensor 200B according to a second sensor embodiment including photocathode 100B, a detection device 210B (e.g., a CCD or a CMOS image sensor) formed on a (second) silicon substrate 211C, and a housing 202 that maintains photocathode 100B at a fixed distance from detection device 210B. As described above with reference to FIG. 2(B), photocathode 100B is characterized by including second boron layer (third layer) 106 disposed directly on illuminated (first) surface 102 of silicon substrate 101, and an anti-reflective material (fourth) layer 107 disposed on second boron layer 106. In this embodiment, housing 202B does not includes a window disposed above photocathode 100, so receiving surface 203B of sensor 200B is formed by an outer (upper) surface of anti-reflective material (fourth) layer 107. Sensor 200B thus has the advantage of being more sensitive (i.e., able to detect lower amounts of light) than sensors with a window owing to no losses due to reflection or absorption by the window. As such, sensor 200B exhibits a relatively high sensitivity from near infrared wavelengths to X-ray wavelengths.

FIG. 5(C) shows a sensor 200C according to a third sensor embodiment including photocathode 100 and a silicon-based detection device 210C (e.g., a CCD or a CMOS image sensor formed on a (second) silicon substrate 211C) that is secured to a housing 202C in a manner similar to that described above with reference to FIG. 5(A).

According to an aspect of the third sensor embodiment, housing 202C includes an upper window portion 204C that is disposed over photocathode 100, and an anti-reflective material layer 207C, which forms to improve receiving surface 203C, is formed on window 204C in order to improve photon capture by sensor 200C. In an alternative embodiment, an additional anti-reflective material layer (not shown) is disposed between photocathode 100 and window 204C (i.e., photocathode 100 is implemented using, for example, photocathode 100B, which is described above with reference to FIG. 2(B)).

In accordance with another aspect of the third sensor embodiment, a (third) boron coating layer 214C is formed directly on a detecting (upper) surface 212 of image sensor 210C using the techniques described above with reference to photocathode 100 to enable efficient absorption of electrons by image sensor 210C that are emitted from photocathode 100. In preferred embodiments, a gap distance G between photocathode 100 and image sensor 210C is between approximately 100 μm and approximately 1 nm. Because boron coating layer 214C improves the efficiency of image sensor 210C for low-energy electrons, a lower accelerating voltage and smaller gap may be used than is typical in prior art devices. The advantage of the lower accelerating voltage and smaller gap is that the spatial resolution of the sensor is improved and the response time is reduced (i.e., the maximum operating frequency is increased). Thermalization of the photoelectrons within the silicon photocathode also improves the spatial resolution of the image sensor.

In other embodiments of the invention, a wafer, reticle or photomask inspection system including an illumination source (e.g., a laser system) for transmitting light (photons) onto a sample/wafer, a sensor (e.g., a photomultiplier, an image intensifier or an EBCCD) that utilizes any of the inventive photocathodes described above to detect photons passing through or reflected by the sample/wafer, and an associated optical system for guiding the light/photons from the illumination source to the sample (wafer, reticle or photomask), and from the sample to the sensor. Examples of these embodiments are shown in FIGS. 6 through 10.

Figure 6:
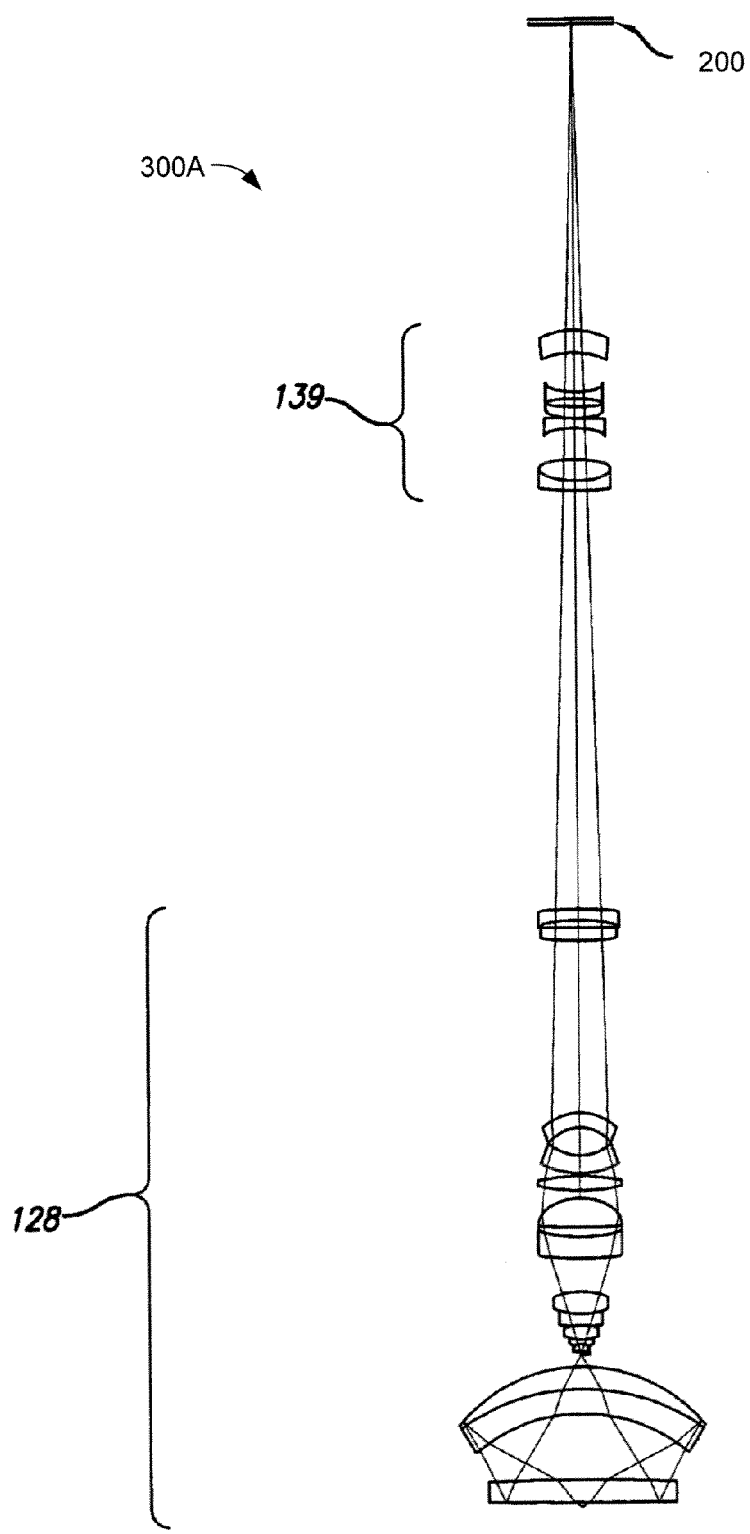
FIG. 6 is a simplified diagram showing an inspection system according to another embodiment of the present invention.

FIG. 6 shows key components of an inspection system 300A with dark-field and bright field inspection modes. The optics utilized by system 300A comprise a high numerical aperture large field-of-view objective lens 128, tube lens 139 for setting or adjusting the magnification and a detector 200, which incorporates a photocathode constructed in accordance with any of the embodiments described above. When operating in dark-field mode the detector 200 incorporates the inventive photocathode in an EBCCD or image intensifier arrangement similar to that shown in any of FIGS. 5(A) to 5(C). More details on other aspects of this inspection system can be found in U.S. Pat. No. 7,345,825, which is incorporated herein by reference in its entirety.

Figure 7A:
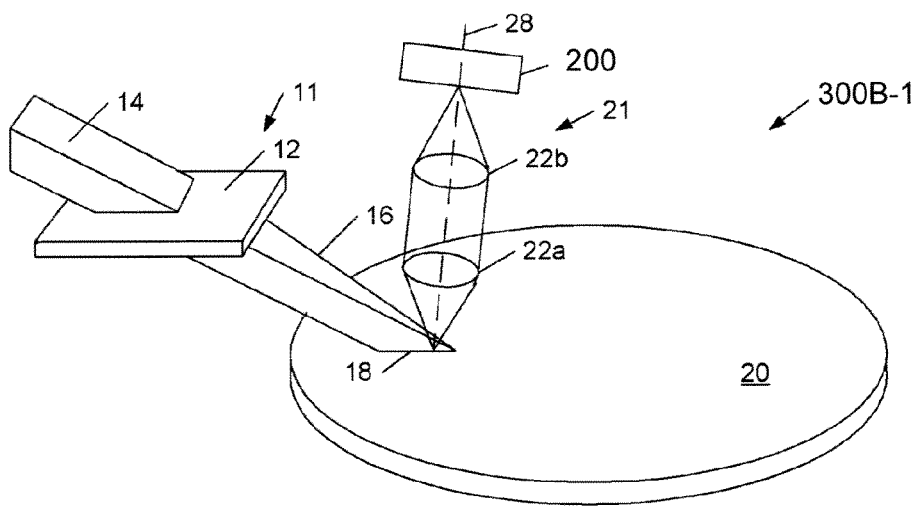
FIGS. 7(A), 7(B), 7(C) and 7(D) are simplified diagrams showing inspection systems according to additional embodiments of the present invention.
Figure 7B:
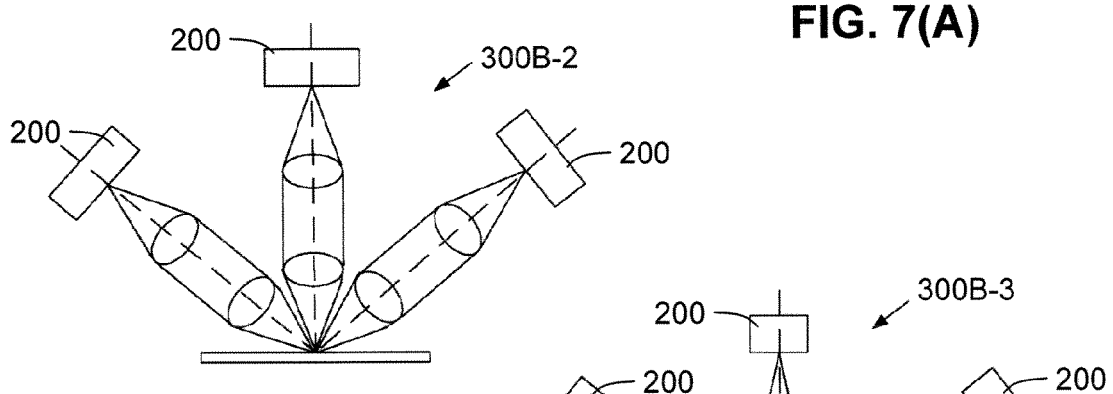
Figure 7C:
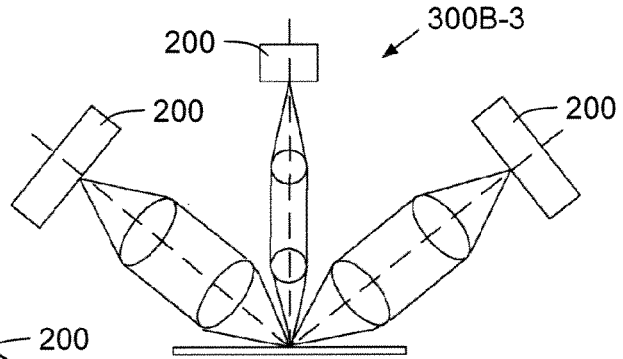
Figure 7D:
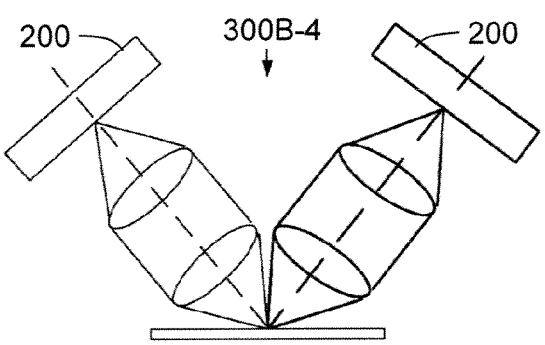

FIGS. 7(A) to 7(D) illustrate aspects of dark-field inspection systems that incorporate the inventive photocathode in accordance with other exemplary embodiments of the present invention. In FIG. 7(A), inspection system 300B-1 illuminates line 18 by light 14/16 that is passed through optics 11 comprising lens or mirror 12 onto the surface 20 of the wafer or photomask (sample) being inspected. Collection optics 21 direct scattered light from that line to sensor 200 using lenses and/or mirrors such as 22a and 22b. The optical axis 28 of the collection optics is not in the illumination plane of line 18. In some embodiments, axis 28 is approximately perpendicular to the line 18. Sensor 200 is an array sensor, such as a linear array sensor, incorporating the inventive photocathode, for example, in accordance with the embodiments illustrated in any of FIGS. 5(A), 5(B) and 5(C). FIGS. 7(B), 7(C) and 7(D) illustrate alternative arrangements of multiple dark-field collection systems (300B-2, 300B-3 and 300B-4, respectively) that incorporate detectors 200 with the inventive photocathode in combination with line illumination such as that shown in FIG. 7(A). More details of these inspection systems can be found in U.S. Pat. No. 7,525,649, which is incorporated herein by reference in its entirety. U.S. Pat. No. 6,608,676, which is also incorporated herein by reference in its entirety, also describes line illumination systems suitable for inspection of unpatterned or patterned wafers.

Figure 8:
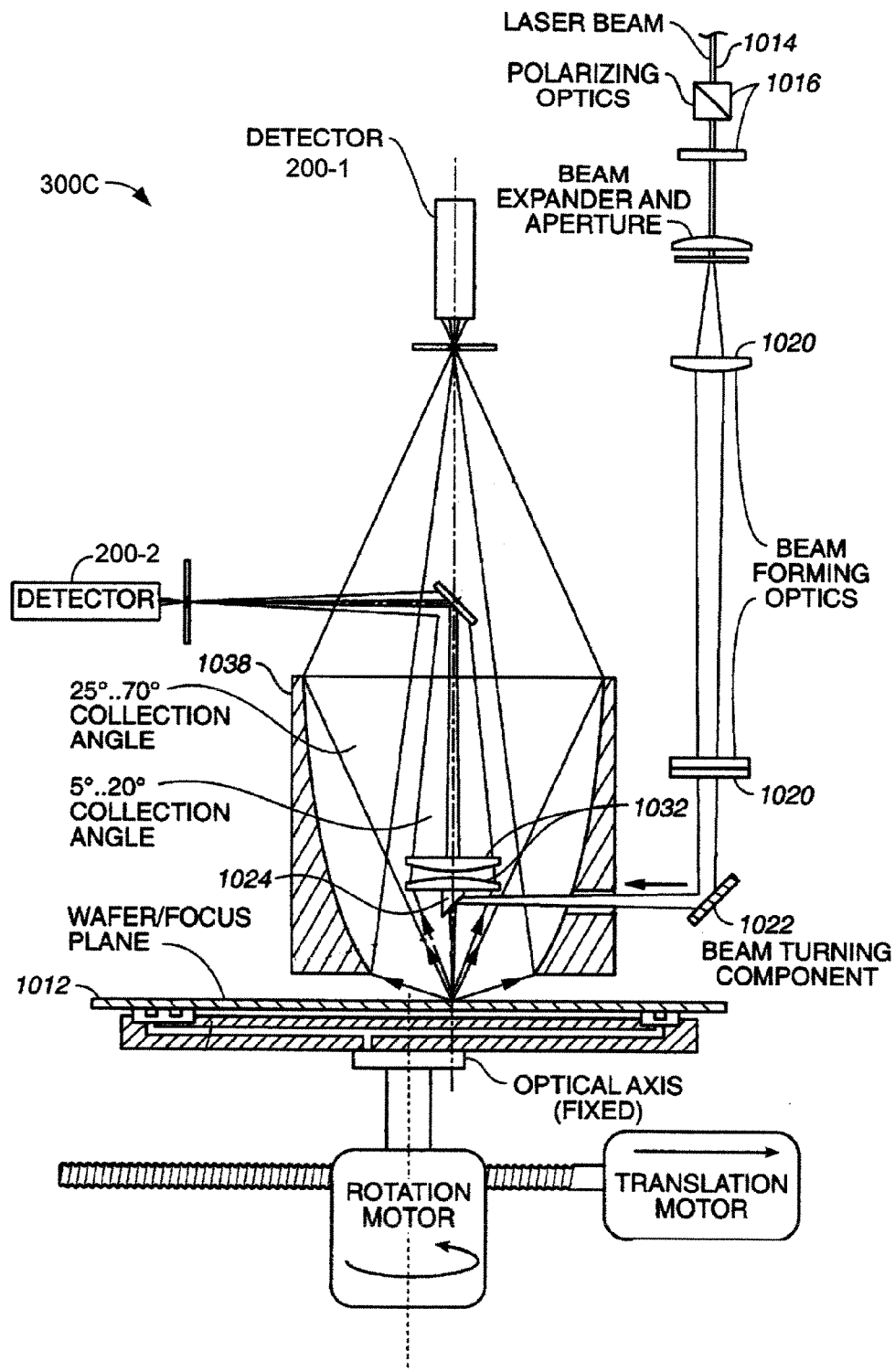
FIG. 8 is a simplified diagram showing another inspection system according to another embodiment of the present invention.

FIG. 8 shows an unpatterned wafer inspection system 300C that incorporates the inventive photocathode in accordance with another exemplary embodiment of the present invention. Light from laser 1014 is directed to wafer 1012 by means of polarizing optics 1016, beam forming optics 1020 and turning mirrors such as 1022 and 1024. Light scattered from the wafer is collected by mirrors and lenses such as 1038 and 1032 and sent to detectors 200-1 and 200-2, which incorporate a photocathode constructed in accordance with any of the embodiments described above. In some embodiments, detectors 200-1 and 200-2 comprise photomultiplier tubes incorporating the inventive photocathode. More details on unpatterned wafer inspection systems can be found in U.S. Pat. No. 6,271,916, which is incorporated herein by reference in its entirety.

Figure 9:
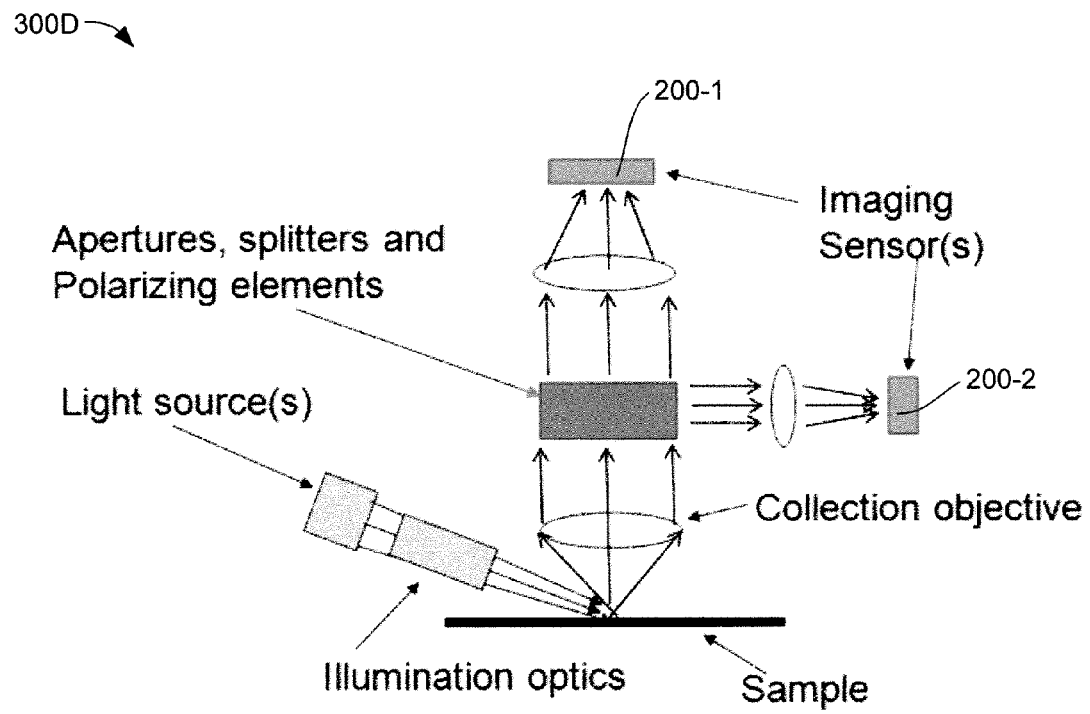
FIG. 9 is a simplified diagram showing another inspection system according to another embodiment of the present invention.

FIG. 9 shows a flood-illumination wafer inspection system 300D in accordance with another alternative embodiment of the present invention. An area of a wafer (sample) is illuminated by an off-axis light source. Light scattered from the wafer is collected by the collection objective, passes one or more apertures, splitters and polarizers and then is directed to one or more image sensors 200-1 and 200-2, which incorporate a photocathode constructed in accordance with any of the embodiments described above. In some embodiments, image sensors 200-1 and 200-2 comprise an EBCCD or an image intensifier incorporating the inventive photocathode. More details of this inspection system can be found in co-owned and copending US Patent Application No. 2013/0016346 entitled "Wafer Inspection" by Romanovsky et al., which is incorporated herein by reference in its entirety. In these inspection system embodiments, the wafer is preferably continuously moving during the inspection. The image sensor used in this embodiment of the invention can advantageously incorporate any of the techniques described in co-owned and co-pending U.S. Patent Application No. 2013/0148112 entitled "Electron-Bombarded Charge-Coupled Device And Inspection Systems Using EBCCD Detectors", which is incorporated herein by reference in its entirety.

Figure 10:
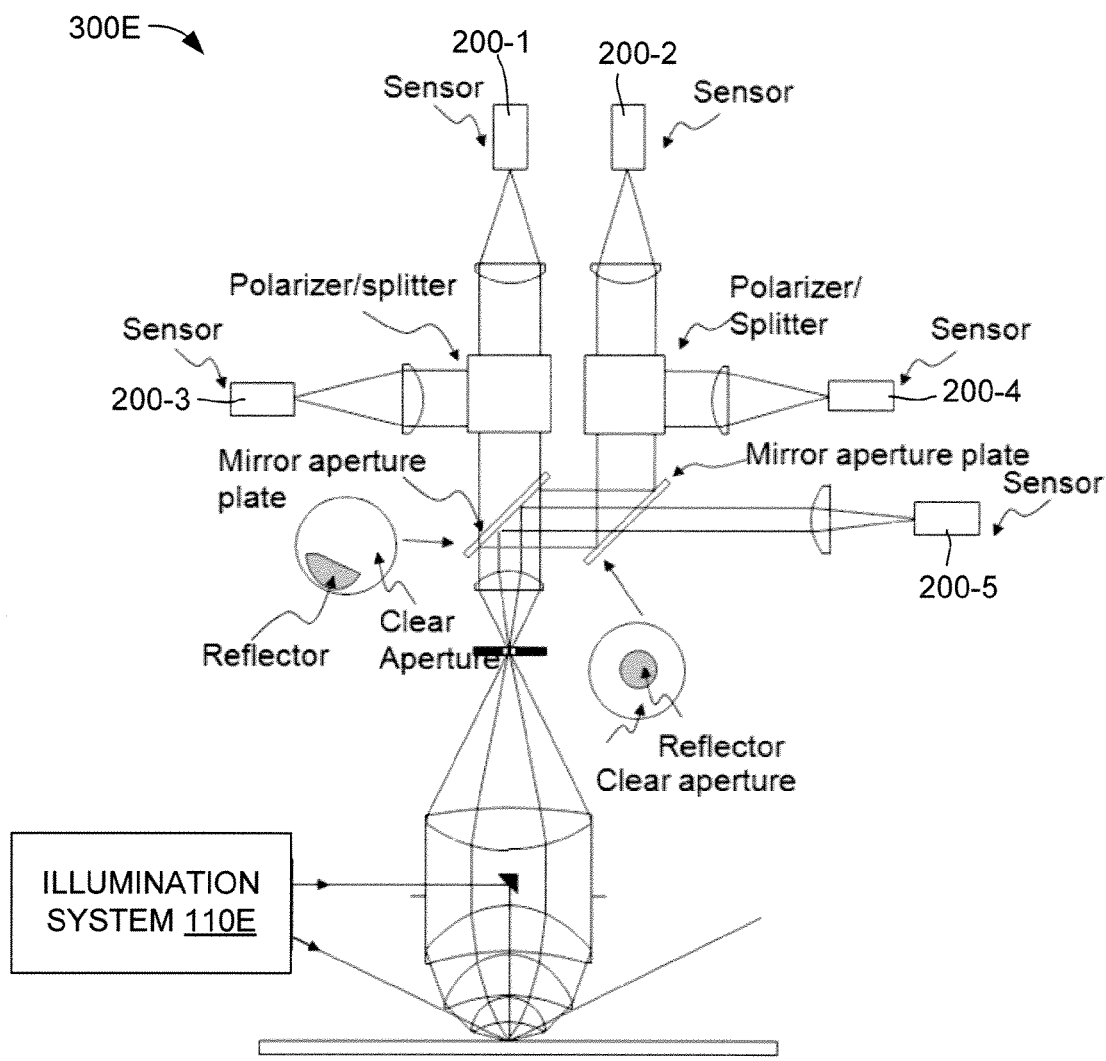
FIG. 10 is a simplified diagram showing another inspection system according to another embodiment of the present invention.
Figure 11:
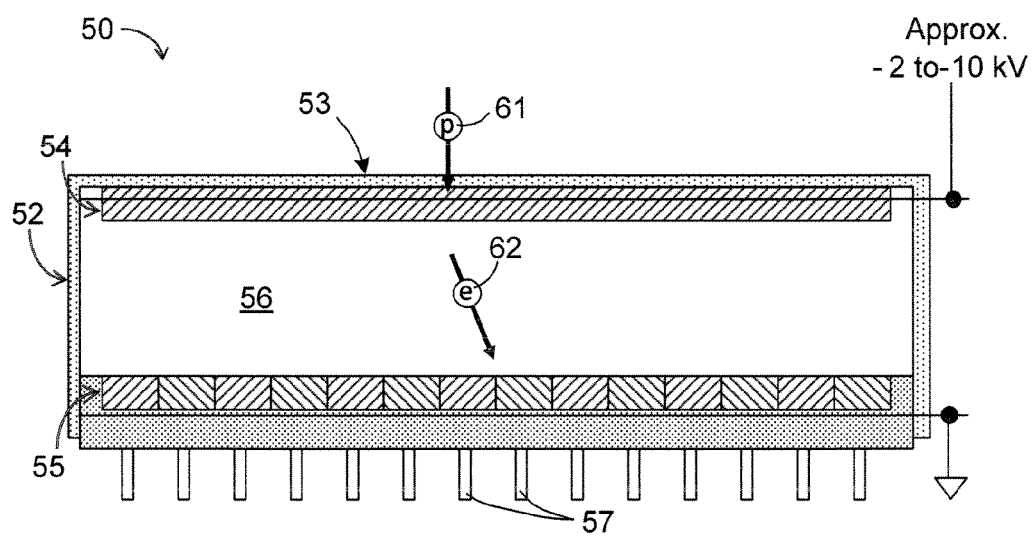
FIG. 11 is a cross-sectional side view illustrating a conventional sensor.

FIG. 10 shows a wafer inspection system 300E in accordance with another alternative embodiment of the present invention. Inspection system 300E includes an illumination subsystem 110E that provides oblique illumination and substantially normal illumination by way of the illustrated optical system, which collects the scattered light and directs that light through various apertures and polarizing beam splitters to multiple sensors 200-1 to 200-5, which incorporate the inventive photocathode in accordance with any of the embodiments described above.

Prior-art image intensifiers and electron-bombarded CCDs have to compromise between sensitivity and spectral bandwidth. At best, good sensitivity is possible only for a narrow range of wavelengths. This invention, by enabling the use of silicon as a photocathode, allows high sensitivity over a wider range of wavelengths. Furthermore, because of the high efficiency and low work-function of the inventive photocathode, image intensifiers, photomultipliers and electron-bombarded CCDs can, in some embodiments, operate with lower accelerating voltages, which in turn improves device lifetime, and increases the maximum operating frequency and/or spatial resolution.

Prior-art silicon photocathodes have an oxide layer on each surface, which impedes the escape of photoelectrons and results in low efficiency. By forming a boron layer on the output surface of the silicon allows electrons to escape more easily resulting in higher efficiency.

An image sensor that combines the inventive photocathode with a boron-coated CCD or CMOS image sensor exhibits higher quantum efficiency in the photocathode combined with the increased sensitivity of the boron-coated CCD.

Dark-field inspection systems incorporating detectors with the inventive photocathode have a combination of high efficiency, very low noise level and high-speed operation that is not achievable with conventional image and light sensors.

Although the present invention has been described with respect to certain specific embodiments, it will be clear to those skilled in the art that the inventive features of the present invention are applicable to other embodiments as well, all of which are intended to fall within the scope of the present invention.

The invention claimed is:

1. A sensor for generating an electric signal in response to photons directed onto a receiving surface, the sensor comprising:
    a photocathode disposed adjacent to the receiving surface for emitting photoelectrons in response to said photons, the photocathode including:
        a silicon substrate having a first surface facing the receiving surface, and a second surface facing away from the receiving surface,
        a first layer consisting essentially of boron disposed directly on the second surface of the silicon substrate, and
        a second layer comprising a low work-function material disposed on the first layer;
    a detection device having a detecting surface facing the second layer, said detection device including means for detecting said photoelectrons emitted by said photocathode, and means for generating said electric signal in response to said detected photoelectrons;
    a housing operably connected between the photocathode and the detection device such that the detecting surface of the detection device is separated from the second layer of the photocathode by an intervening gap region; and
    means for generating an electric field between the photocathode and the detection device such that electrons emitted from the photocathode into the gap region are accelerated toward the detection device by the electric field.

2. The sensor of claim 1, wherein the low work-function material comprises one of an alkali metal and an alkali metal oxide.

3. The sensor of claim 2, wherein the low work-function material comprises cesium.

4. The sensor of claim 1, wherein the first layer has a thickness in the range of approximately 1 nm to 5 nm.

5. The sensor of claim 1, wherein said sensor comprises one of an image intensifier, an electron-bombarded charge-coupled device (EBCCD) and a photomultiplier.

6. The sensor of claim 1, further comprising a third layer consisting essentially of boron disposed directly on the first surface of the silicon substrate.

7. The sensor of claim 6, further comprising a fourth layer comprising an anti-reflective material disposed on the third layer.

8. The sensor of claim 7, wherein the receiving surface of the sensor comprises an outer surface of the fourth layer.

9. The sensor of claim 1, wherein the receiving surface comprises a layer of anti-reflective material disposed on a window.

10. The sensor of claim 1, wherein the detection device comprises a second silicon substrate and includes a boron layer disposed directly on the detecting surface of the silicon substrate.

11. An inspection system comprising:
    an illumination source for transmitting photons onto a sample;
    a sensor for detecting photons from the sample; and
    an optical system for guiding the photons from the illumination source to the sample, and from the sample to a receiving surface of the sensor,
    wherein the sensor comprises:
        a photocathode disposed adjacent to the receiving surface for emitting photoelectrons in response to said photons, the photocathode including:
            a monocrystalline silicon substrate having a first surface directed toward the optical system, and a second surface facing away from the optical system,
            a first layer consisting essentially of boron disposed directly on the second surface of the silicon substrate, and
            a second layer comprising a low work-function material disposed on the first layer;
        a detection device having a detecting surface facing the second layer, said detection device including means for detecting said photoelectrons emitted by said photocathode, and means for generating said electric signal in response to said detected photoelectrons;
        a housing operably connected between the photocathode and the detection device such that the detecting surface of the detection device is separated from the second layer of the photocathode by an intervening gap region; and
        means for generating an electric field between the photocathode and the detection device such that electrons emitted from the photocathode into the gap region are accelerated toward the detection device by the electric field.

12. The inspection system of claim 11, wherein said sensor comprises one of an image intensifier, an electron-bombarded charge-coupled device (EBCCD) and a photomultiplier.

* * * * *